(12) United States Patent
Chen et al.

(10) Patent No.: US 10,048,264 B2
(45) Date of Patent: Aug. 14, 2018

(54) LUNG CANCER BIOMARKER

(71) Applicants: Academia Sinica, Taipei (TW); National Taiwan University, Taipei (TW)

(72) Inventors: Shui-Tein Chen, Taipei (TW); Chong-Jen Yu, Taipei (TW); Potprommanee Laddawan, Taipei (TW); Haou-Tzong Ma, Taipei (TW)

(73) Assignees: ACADEMIA SINICA, Taipei (TW); NATIONAL TAIWAN UNIVERSITY, Taipei (TW)

(*) Notice: Subject to any disclaimer, the term of this patent is extended or adjusted under 35 U.S.C. 154(b) by 98 days.

(21) Appl. No.: 14/538,888

(22) Filed: Nov. 12, 2014

(65) Prior Publication Data

US 2016/0109452 A1 Apr. 21, 2016

(30) Foreign Application Priority Data

Oct. 16, 2014 (TW) .............................. 103135789 A

(51) Int. Cl.
*G01N 33/574* (2006.01)
*C07K 14/47* (2006.01)
(52) U.S. Cl.
CPC ... *G01N 33/57423* (2013.01); *C07K 14/4706* (2013.01); *G01N 2333/4706* (2013.01); *G01N 2800/52* (2013.01)

(58) Field of Classification Search
CPC ..................... G01N 33/57423; C07K 14/4705
See application file for complete search history.

(56) References Cited

U.S. PATENT DOCUMENTS

| 2007/0065827 A1* | 3/2007 | Pauloski | C12Q 1/6886 435/6.14 |
| 2010/0070191 A1* | 3/2010 | Gold | G01N 33/57423 702/19 |
| 2013/0045873 A1* | 2/2013 | Hood | G01N 33/68 506/2 |

OTHER PUBLICATIONS

Arya et al. "Lung Cancer and Its Early Detection Using Biomarker-Based Biosensors," Chem. Rev., vol. 111, pp. 6783-6809, published Jul. 20, 2011.*

* cited by examiner

*Primary Examiner* — Tracy Vivlemore
*Assistant Examiner* — Nam P Nguyen
(74) *Attorney, Agent, or Firm* — Bacon & Thomas, PLLC

(57) ABSTRACT

The present invention relates to a lung cancer biomarker for diagnosing early stage lung cancers or predicting prognosis of lung cancers, which comprises a GM2AP protein. The present invention also relates to a method for diagnosing early stage lung cancers or predicting prognosis of lung cancers in vitro by detection of the biomarker.

10 Claims, 15 Drawing Sheets

A

SEQUENCE LISTING

<160> NUMBER OF SEQ ID NOS: 3

<210> SEQ ID NO 1
<211> LENGTH: 193
<212> TYPE: PRT
<213> ORGANISM: Homo sapiens

<400> SEQUENCE: 1

Met Gln Ser Leu Met Gln Ala Pro Leu Leu Ile Ala Leu Gly Leu Leu

```
            1               5                  10                 15
Leu Ala Ala Pro Ala Gln Ala His Leu Lys Lys Pro Ser Gln Leu Ser
                20                 25                 30

Ser Phe Ser Trp Asp Asn Cys Asp Glu Gly Lys Asp Pro Ala Val Ile
         35                 40                 45

Arg Ser Leu Thr Leu Glu Pro Asp Pro Ile Ile Val Pro Gly Asn Val
         50                 55                 60

Thr Leu Ser Val Met Gly Ser Thr Ser Val Pro Leu Ser Ser Pro Leu
 65                 70                 75                 80

Lys Val Asp Leu Val Leu Glu Lys Glu Val Ala Gly Leu Trp Ile Lys
                 85                 90                 95

Ile Pro Cys Thr Asp Tyr Ile Gly Ser Cys Thr Phe Glu His Phe Cys
                100                105                110

Asp Val Leu Asp Met Leu Ile Pro Thr Gly Glu Pro Cys Pro Glu Pro
                115                120                125

Leu Arg Thr Tyr Gly Leu Pro Cys His Cys Pro Phe Lys Glu Gly Thr
     130                135                140

Tyr Ser Leu Pro Lys Ser Glu Phe Val Val Pro Asp Leu Glu Leu Pro
145                150                155                160

Ser Trp Leu Thr Thr Gly Asn Tyr Arg Ile Glu Ser Val Leu Ser Ser
                165                170                175

Ser Gly Lys Arg Leu Gly Cys Ile Lys Ile Ala Ala Ser Leu Lys Gly
                180                185                190

Ile

<210> SEQ ID NO 2
<211> LENGTH: 193
<212> TYPE: PRT
<213> ORGANISM: Homo sapiens

<400> SEQUENCE: 2

Met Gln Ser Leu Met Gln Ala Pro Leu Leu Ile Ala Leu Gly Leu Leu
 1               5                  10                 15

Leu Ala Ala Pro Ala Gln Ala His Leu Lys Lys Pro Ser Gln Leu Ser
                20                 25                 30

Ser Phe Ser Trp Asp Asn Cys Asp Glu Gly Lys Asp Pro Ala Val Ile
         35                 40                 45

Arg Ser Leu Thr Leu Glu Pro Asp Pro Ile Val Val Pro Gly Asn Val
         50                 55                 60

Thr Leu Ser Val Val Gly Ser Thr Ser Val Pro Leu Ser Ser Pro Leu
 65                 70                 75                 80

Lys Val Asp Leu Val Leu Glu Lys Glu Val Ala Gly Leu Trp Ile Lys
                 85                 90                 95

Ile Pro Cys Thr Asp Tyr Ile Gly Ser Cys Thr Phe Glu His Phe Cys
                100                105                110

Asp Val Leu Asp Met Leu Ile Pro Thr Gly Glu Pro Cys Pro Glu Pro
                115                120                125

Leu Arg Thr Tyr Gly Leu Pro Cys His Cys Pro Phe Lys Glu Gly Thr
     130                135                140

Tyr Ser Leu Pro Lys Ser Glu Phe Val Val Pro Asp Leu Glu Leu Pro
145                150                155                160

Ser Trp Leu Thr Thr Gly Asn Tyr Arg Ile Glu Ser Val Leu Ser Ser
                165                170                175

Ser Gly Lys Arg Leu Gly Cys Ile Lys Ile Ala Ala Ser Leu Lys Gly
```

```
                    180                 185                 190
Ile

<210> SEQ ID NO 3
<211> LENGTH: 14
<212> TYPE: PRT
<213> ORGANISM: Homo sapiens

<400> SEQUENCE: 3

Pro Ile Val Val Pro Gly Asn Val Thr Leu Ser Val Val Gly
1               5                   10
```

LUNG CANCER BIOMARKER

BACKGROUND OF THE INVENTION

Field of the Invention

The present invention relates to a lung cancer biomarker for diagnosing early stage lung cancers or predicting prognosis of lung cancers, which comprises a GM2AP protein. The present invention also relates to a method for diagnosing early stage lung cancers or predicting prognosis of lung cancers in vitro by detection of the biomarker.

Description of the Related Art

Lung cancer is the leading cause of cancer-related deaths worldwide, accounting for 28% of all male cancer deaths and 26% of all female cancer deaths in the United States in 2013.[1] Lung cancer can typically be grouped into two main categories:

small-cell lung cancer (SCLC) and non-small cell lung cancer (NSCLC), accounting for 15% and 85% of lung cancers, respectively. NSCLC consists of three major histological subtypes: adenocarcinoma, squamous cell carcinoma and large cell carcinoma.[2] Due to lack of effective early detection tools and ineffective treatments for the advanced stages, the 5-year survival rate of lung cancer is only 15%.[3,4] Therefore, early detection is crucial and beneficial for lung cancer patients to receive appropriate and potentially curative treatments.

Tantipaiboonwong et al. first used two-dimensional gel electrophoresis (2-DE) and matrix-assisted laser desorption ionization-time of flight mass spectrometry (MALDI-TOF/MS) in search of urinary biomarkers of lung cancer and reported six up-regulated protein spots and three down-regulated protein spots in lung cancer urine samples compared to the controls.[5] Among these up-regulated protein spots, the expression of GM2AP level in lung cancer patients was 2.5-4.0 folds higher than that in healthy volunteers. This was consistent with the 2-DE and Western blotting results obtained by Potprommanee et al.[6]

GM2-activator protein (GM2AP) is a small monomeric protein containing a single site for Asn linked glycosylation.[7] It is first synthesized as a precursor which is then glycosylated, modified and cleaved at $^{32}$Ser to be in the mature form. Mature GM2AP is a glycoprotein with molecular mass of 17.6 kDa in its deglycosylated form.[8] Acting as a cofactor, GM2AP contains at least three functional features including a hydrophobic pocket called the β-cup structure, an oligosaccharide binding site, and an area that interacts with Hex A.[9,10] The area that interacts with Hex A contributes to the degradation of GM2 ganglioside to GM3 by lysosomal β-hexminidase A (Hex A).[11,12] However, only one-third of the synthesized of GM2AP is secreted.[13,10] Cells can recapture the GM2AP via a carbohydrate-independent mechanism by various cells such as epidermal keratinocytes and fibroblast cells.[10] A lack of the functional GM2AP is a cause of the abnormal accumulation of GM2 ganglioside in tissues of patients with the AB variant of GM2 gangliosidosis disease (a severe lysosomal storage disorder).[14] The inherited deficiency of GM2AP was also related to the changing level of ganglioside and tumor associated gangliosides involving in cancer progression. Tumor-associated gangliosides are a result of initial oncogenic transformation and play a role in the induction of invasion and metastasis.[15,16] Tumor cells synthesized and shed gangliosides into their microenvironments, and this leads to elevated levels of tumor-associated gangliosides in the serum.[17,18,19] Moreover, gangliosides are known to exhibit regulatory roles in cell growth, adhesion, cell-cell interactions and signal transduction.[20] However, no study has been carried out to investigate the levels of GM2AP and its clinical roles in large number of urine, or biological samples besides urine from patients with lung cancer.

SUMMARY OF THE INVENTION

The object of the present invention is to provide a lung cancer biomarker, which can be detected in vitro by a non-invasive way, and useful for auxiliary diagnosis, treatment and prognosis.

To achieve the object, the present invention provides a lung cancer biomarker for diagnosing early stage lung cancers or predicting prognosis of lung cancers, comprising a GM2AP protein (SEQ ID No: 1 or SEQ ID No: 2). Particularly, the present invention provides a glycosylated GM2AP protein, which comprises a peptide fragment (SEQ ID No: 3) binding to a polysaccharide structure (Hex)$_3$(HexNAc)$_2$(Fuc)$_1$.

In a preferred embodiment, when the amount of said lung cancer biomarker in urine of a lung cancer patient is higher than 0.234 ng/mL, the possibility that the lung cancer patient suffers from an early stage lung cancer is higher, especially a stage I or stage II lung cancer. Particularly, when the amount of said lung cancer biomarker in urine of a lung cancer patient is higher than 0.234 ng/mL, the best true positive and true negative can be achieved, and healthy people and cancer patients can be separated. Further examinations can be made based on the results, and other unnecessary and complicated examinations can be avoided.

In a preferred embodiment, when the amount of said lung cancer biomarker in serum of a lung cancer patient is higher than 0.342 ng/mL, the possibility that the lung cancer patient suffers from an early stage lung cancer is higher, especially a stage I or stage II lung cancer. Particularly, when the amount of said lung cancer biomarker in serum of a lung cancer patient is higher than 0.342 ng/mL, the best true positive and true negative can be achieved, and healthy people and cancer patients can be separated. Further examinations can be made based on the results, and other unnecessary and complicated examinations can be avoided.

In a preferred embodiment, when the IHC score of said lung cancer biomarker in lung tissue section of a lung cancer patient is 2, the lung cancer patient has a worse prognosis, especially when the lung cancer patient suffers from an early stage non-small cell lung cancer. Particularly, the lung cancer patient suffers from a stage I or stage II non-small cell lung cancer. In this invention, predicting prognosis of lung cancers means predicting the overall survival and disease-free survival of the patient. The IHC score is scored according to the percentage of the positively stained cells in the field of fixation: 0 (0%); 1 (1-20%); 2 (20-100%).

The present invention also provides a method for diagnosing early stage lung cancers or predicting prognosis of lung cancers in vitro, comprising the following steps:
(1) providing a sample from a patient;
(2) detecting the amount of the above-mentioned lung cancer biomarker in said sample; and
(3) assessing the amount of the lung cancer biomarker according to claim 1 in said sample to diagnose whether the patient suffers from an early stage lung cancer or predict the lung cancer prognosis of the patient.

In a preferred embodiment, the sample is an urine, serum or tissue section sample from the patient. Preferably, the tissue section sample is a lung tissue section sample. The sample is obtained from human or animal, and used for in vitro detection.

In a preferred embodiment, the step (2) is detected by immunoanalysis or mass spectrometry. Preferably, the immunoanalysis comprises Western blotting, flow cytometry, immunohistochemistry staining, ELISA. Also preferably, the mass spectrometry is processed through multiple reaction monitoring by a mass spectrometer for relative quantification, and a general mass spectrometer or a portable mass spectrometer can be used for detection. In order to set up an associated detection system in a hospital, a portable mass spectrometry is preferred.

In a preferred embodiment, when the amount of said lung cancer biomarker in urine of a lung cancer patient is higher than 0.234 ng/mL, the possibility that the lung cancer patient suffers from an early stage lung cancer is higher, especially a stage I or stage II lung cancer.

In a preferred embodiment, when the amount of said lung cancer biomarker in serum of a lung cancer patient is higher than 0.342 ng/mL, the possibility that the lung cancer patient suffers from an early stage lung cancer is higher, especially a stage I or stage II lung cancer.

In a preferred embodiment, when the IHC score of said lung cancer biomarker in lung tissue section of a lung cancer patient is 2, the lung cancer patient has a worse prognosis, especially when the lung cancer patient suffers from an early stage non-small cell lung cancer. Particularly, the lung cancer patient suffers from a stage I or stage II non-small cell lung cancer. In this invention, predicting prognosis of lung cancers means predicting the overall survival and disease-free survival of the patient.

From above, it should be clear that the present invention provides a lung cancer biomarker GM2AP, which plays a role in lung cancer development and can be used in auxiliary diagnosis for lung cancer. It is also a good prognosis factor for early stage NSCLC.

DETAILED DESCRIPTION OF THE PREFERRED EMBODIMENTS

Figure 1A:
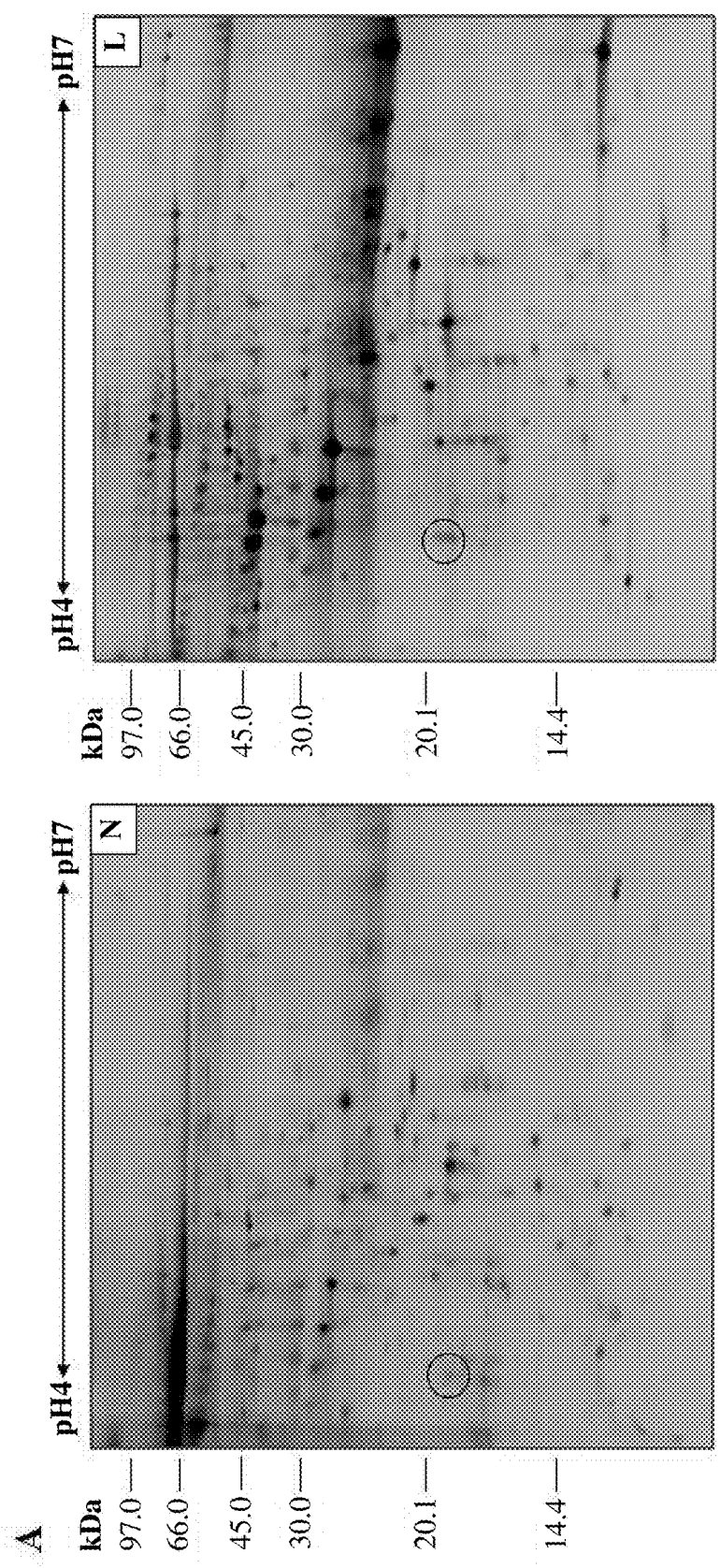
FIG. 1A represents the 2-DE analysis images of pooled urine samples of healthy controls (N) and lung cancer patients (L).

The following examples are presented to demonstrate the present invention. These examples are in no way to be construed as a limitation on the invention. The disclosure would enable those skilled in the art to practice the present invention without engaging in undue experimentation. All recited publications are incorporated herein by reference in their entirety.

Preparations of Group I Urine Samples (Thailand)

Human urine samples from 44 healthy individuals and 48 lung cancer patients (n=25 for adenocarcinoma, n=15 for small cell lung cancer, n=4 for squamous cell carcinoma, n=4 for other types of carcinoma) were provided by Maharaj Nakron Chiang Mai Hospital, Chiang Mai, Thailand. The collections of urine samples were carried out with permission from the volunteers and approved by the Research Ethics Committee, Faculty of Medicine, Chiang Mai University for research purpose only. Urine samples were obtained from lung cancer patients aged 28-74 (mean age: 53.3) who had been diagnosed as lung cancer at advanced stages (stage III and stage IV for non-small cell lung cancers, limited and extensive stage for small cell lung cancer), including 33 males and 15 females. The patients had no disorder of renal function as revealed by normal urine creatinine and blood urea nitrogen. Healthy volunteer urine samples were obtained from healthy volunteers aged 25-74 years. The tumor stage of the lung cancer was determined according to the International System for Staging Lung Cancer.[21] The clinical information for lung cancer and information of healthy controls urine samples are shown in Table 1. All urine samples were collected in early morning (the first urination after waking up) in a sterile tube. Then, the urine samples were subsequently centrifuged at 12000×g for 30 min at 4° C. to remove cellular contamination and debris. The supernatants were lyophilized and stored at −80° C. until further analysis.

Preparations of Group II Urine and Serum Samples (Taiwan)

Urine and serum samples from 133 lung cancer patients, before receiving any anticancer treatment, were consecutively collected at National Taiwan University Hospital, Taipei, Taiwan from January, 2012 to June, 2013. The study population included 61 (46%) male and 72 (54%) female patients, with a mean age of 62 (range: 30-80). Regarding with the histology type, it included 111 adenocarcinoma patients, 4 small cell lung cancer patients, 11 squamous cell carcinoma patients and 7 other types of carcinoma patients. There were 18 patients in stage I, 6 patients in stage II, 25 patients in stage III and 84 patients in stage IV (see Table 2). The samples of control group were collected from the health screen department, 26 healthy volunteers donated urine samples and 30 healthy volunteers donated serum samples.

Preparations of Pathologic Tissue Specimens (Taiwan)

In addition, paraffin-embedded pathologic tissue specimens from 143 NSCLC patients were obtained from the archives of the Department of Pathology, National Taiwan University Hospital, Taipei, Taiwan. The selected cases were diagnosed based on a distinctive pathologic diagnosis of NSCLC, and the patients underwent surgical resection for tumor with curative intent without preoperative chemotherapy or radiotherapy from January, 2002 to December, 2006. The clinicopathological features, such as age, gender, cancer stage, date of recurrence, date of decease, were collected retrospectively by medical chart record and cancer registry system. There were 79 (55%) male and 64 (45%) female patients with a mean age of 65.3. There were 60 patients in stage I, 61 patients in stage II, 20 patients in stage III and 2 patients in stage IV (see Table 3). Lung tissues from unaffected parts of the lung cancer patients were used as controls.

For the urine and serum samples from Group II patients and the pathologic tissue specimens, tumor stage was defined according to the American Joint Committee on Caner/International Union against Cancer Tumor-node-metastasis (TNM) classification system.[22] The study was approved by the institute research ethic committee of National Taiwan University Hospital (NTUH REC no. 201103074RC).

Two-Dimensional Electrophoresis (2-DE)

Urine samples were loaded into the centricon tube (MW cut off at 3 kDa) (Millipore Corpore Corporate, MA, USA) and centrifuged at 5000×g at 4° C. for 1 h. Distilled water was added to the centricon tube to partially desalt and elute out some interference. Urine samples were then passed through a PD-10 desalting column (Amersham Biosciences, UK) and eluted with 10 mM phosphate buffer, pH 7.5. The fraction containing proteins were collected and lyophilized. The concentration of urine protein was determined by spectrophotometry using Bio-Rad protein microassay based on the method of Bradford (Bio-Rad Laboratories, CA, USA). 200 μg of urine samples were dissolved in IEF buffer that contained 7 M urea, 2 M thiouria, 4% CHAPS, 1% dithiothreitol (DTT) and 0.5% carrier ampholytes and 0.002% bromophenol blue. The samples were sonicated, centrifuged and then applied onto IPG strip of pH 4-7 (18 cm, Amersham Biosciences, Uppsala, Sweden) for 2-DE analysis. To determine the glycan structure of GM2AP, 1000 μg of urine samples were loaded onto a narrow range IPG strip of 3-5.6 (18 cm, Amersham Biosciences, Uppsala, Sweden) for preparative analysis. The IPG strips were subsequently rehydrated on the IPGphor IEF system (Amersham Biosciences, UK) at 20° C. with a gradual increase of voltage (30 V for 14 h, 100 V for 1 h, 250 V for 1 h, 500 V for 1 h, 1000 V for 1 h, 3000 V for 1 h, 5000 V for 1 h, and focusing at 8000 V for up to 64000 Vh). After IEF, the proteins on the strip were initially equilibrated for 15 min in equilibration buffer I (containing 6 M urea, 30% glycerol, 2% SDS, 2% w/v DTT, bromophenol blue, and 50 mM Tris-HCl, pH 8.8) and for additional 15 min in equilibration buffer II (equivalent to equilibration buffer I but containing 2.5% w/v iodoacetamide (IAA) instead of DTT). The IPG strip was placed on top of the 15% polyacrylamide gel (18×18 cm, 1.5 mm) and covered with 0.5% agarose. The 2-DE separation was electrophoresed at 45 mA per gel at 4° C. until the bromophenol blue dye front reached the bottom of the gel. After electrophoresis, the protein in the gels were strained with SYPRO® Ruby and scanned using a Typhoon 9200 image scanner (Amersham Biosciences, Uppsala, Sweden) at a wavelength of 610 nm After scanning, the gel images were analyzed by the Image Master™ 2D Platinum software version 5.0 (Amersham Biosciences, Uppsala, Sweden).

In-Gel Enzymatic Digestion

Protein spots were manually excised from the gels, washed twice with 50% acetonitrile (ACN) in 25 mM ammonium bicarbonate, pH 8.0 for 15 min each and dried in 100% ACN. The proteins in the spots were reduced with 10 mM DTT in 25 mM ammonium bicarbonate at 56° C. for 45 min, and alkylated with 55 mM IAA at room temperature for 30 mM in the dark. The gel pieces were washed twice with 50% ACN in 25 mM ammonium bicarbonate buffer for 15 mM each and dried in 100% ACN. Dried gel pieces were swollen in 25 mM ammonium bicarbonate containing trypsin and chymotrypsin and incubated at 37° C. for at least 16 h. Peptides were subsequently extracted three times with 50% ACN in 1% trifluoroacetic acid (TFA). The extracted solutions were combined and dried using a SpeedVac concentrator (Labogene Aps, Lynge, Denmark). The digested peptides were desalted with a C18 ZipTip (Millipore, Bedford, Mass., USA). Bound peptides were eluted from the ZipTip with 50% ACN in 0.1% TFA.

Western Blotting

15 μg of protein eluted from urine and serum samples were solved in sample buffer composed of 50 mM Tris pH 8.0, 10% glycerol, 2% SDS, betamercaptoethanol and 0.1% bromophenol blue and applied in each lane onto 14% SDS-PAGE. After SDS-PAGE, proteins were transferred onto polyvinylidene fluoride (PVDF) (Millipore, Bedford, Mass., USA) membranes and blocked with 5% BSA in PBS containing 0.05% Tween 20 (PBST) at 37° C. overnight or at room temperature for 2 hours. The membrane was incubated with rabbit polyclonal anti-human GM2AP primary antibody (1:1000 dilution, Abcam, Cambridge, UK) at room temperature for 2 hours, followed by an anti-rabbit HRP-conjugated secondary antibody (1:5000 dilution, Abcam, Cambridge, UK) at room temperature for 1 hour. The blot was detected with an enhanced chemiluminescence Western blotting detection system (ECL™ kit; PerkinElmer) and exposed to Fujifilm LAS-4000 Luminescent Image Analyzer (FUJIFILM Corporation, Japan).

Lectin Staining

After Western blotting, the PVDF membranes were washed three times with PBST and incubated with 5% BSA in PBST for 2 h at room temperature. The membranes were washed three times with PB ST, followed by staining with 10 μg/mL biotin-conjugated aleuria aurantia lectin (AAL) (Burlingame, Calif., USA) for 2 h at room temperature and washed three times with PB ST. Then, the membranes for lectin blotting were incubated with streptavidin-conjugated HRP (10 μg/mL) for 1 h and washed three times with PBST. The membranes were developed with an enhanced chemiluminescence Western blotting detection system.

ELISA Assay

The GM2AP level was assayed using commercially available sandwich enzymelinked immunosorbent assay kits (Uscn Life Science Inc., Wuhan, PRC). The sensitivity limit of the GM2AP assay was 0.156-10 ng/mL. The analyses were performed in duplicate according to the manufacturer's instructions.

Electroelution for Intact Protein Mass Determination

The GM2AP spots of lung cancer were excised from 2-DE gels and extracted by electroelution using Midi GeBAflex-tube (MW cut off at 3.5 kDa) (Gene Bio-Application, Israel) according to instruction manual provided by the manufacturer. Following electroelution, salts, SDS and dye were removed by dialysis using the same electroelution tubes. The proteins were then concentrated in a vacuum centrifuge for subsequent MALDI-TOF/MS analysis to determine precise molecular mass of GM2AP. Protein was identified by comparison of the observed mass with the predicted mass obtained from the Swiss-Prot entries for those proteins that had been identified by MALDI-TOF peptide mass fingerprinting.

MALDI-TOF Mass Analysis

For mass spectrum analysis, 1 μL of each protein sample were mixed with equal volume of matrix solution consisting of 2,5-dihydroxybenzoic acid (50 nmol/μL in 50% ACN). 1 μL of the resulting mixture was spotted onto a 384-well MALDI target plate and allowed to air dry at room temperature. After crystallization, the sample was deposited manually on top of the matrix and vacuum dried. Analysis was performed on an Ultraflex II MALDI-TOF/TOF mass spectrometer (Bruker Daltonik GmbH, Bremen, Germany). Mass spectra were obtained in the range of mass to charge ratio (m/z) from 10,000 to 30,000.

NanoLC-MS/MS Analysis

High resolution and high mass accuracy nanoflow LC-MS/MS experiments were performed on a LTQ Orbitrap XL ETD mass spectrometer (Thermo Fisher Scientific, San Jose, Calif., USA) equipped with a nanoelectrospray ion source (New Objective, Inc.), an Agilent 1100 Series binary high-performance liquid chromatography pump (Agilent Technologies), and a Famos autosampler (LC Packings). The digestion solution (6 μL) was injected onto a self packed precolumn (150 μm I.D.×30 mm, 5 μm, 200 Å) operating at a flow rate of 10 μL/min Chromatographic separation was performed on a self packed reversed phase C18 nano-column (75 μm I.D.×200 mm, 3 μm, 200 Å) using 0.1% formic acid in water as mobile phase A and 0.1% formic acid in 80% ACN as mobile phase B operated at 300 nL/min flow rate. Electrospray voltage was maintained at 1.8 kV and capillary temperature was set at 200° C. Survey full-scan MS conditions were at mass range (m/z) of 320-2000 and the resolution of the mass spectrometer was set to 30,000. The three most intense ions were sequentially isolated for Higher-energy C-trap Dissociation (HCD) at resolution of 7500 with normalized collision energy (NCE) 28. For protein identification, the MS and MS/MS ion data were annotated with the in-house MASCOT search engine, assuming that peptides were monoisotopic, oxidized at methionine residues, and carbamidomethylated at cysteine residues. Trypsin plus chymotrypsin enzyme with 5 miss cleavages was allowed, and peptide mass tolerances of 5 ppm and 0.01 Da were used for the MS and MS/MS ions search. Each search was performed the Swiss-Prot Human database. For the glycan analysis, HCD was easier to generate $Y_1$ and oxonium ions. The glycopeptides were manually identified by the presence of glycan-specific oxonium ions in the HCD tandem mass spectra.

Immunohistochemistry (IHC) Staining

The tissue slides were deparaffinized in xylene, rehydrated through graded alcohol, immersed in 3% hydrogen peroxide at 37° C. for 10 minutes to block endogenous peroxidase activity. Subsequently, the slides were incubated with rabbit anti-GM2AP antibody (Abcam, Cambridge, UK) at 4° C. overnight. The slides were sequentially incubated with a secondary antibody (Abcam, Cambridge, UK) at room temperature for 1 hour and stained with DAB (3,3-diaminobenzidine). Finally, the sections were counterstained with hematoxylin. ImageScope software (Aperio Technologies, Vista, Calif., USA) is used for morphometry determination on entire tissue sections stained with antibodies against GM2AP. IHC detection was used to determine the GM2AP levels. The IHC score is scored according to the percentage of the positively stained cells in the field of fixation: 0 (0%); 1 (1-20%); 2 (20-100%).

Statistical Analyses

Statistical analysis was performed using the SPSS for Windows version 17.0 (SPSS Inc, Chicago, Ill.). Paired samples t-test and one-way analysis of variance (ANOVA) were used to analyze the GM2AP expression in different groups. Receiver operating characteristic (ROC) curves displayed the trade-off between sensitivity and specificity for biomarkers differentiating between patients and healthy volunteers. The correlation between GM2AP expression and clinicopathologic features of lung cancer patients was evaluated by the Chi-square test or Fisher exact test. Univariate and multivariate survival analyses were performed using the Cox proportional hazards regression model. Survival curves were obtained with the Kaplan-Meier method. Differences were considered statistically significant when P value was less than 0.05.

EXAMPLES

Example 1

Differential Expression Profiles of GM2AP in Urine from Lung Cancer Patients and Healthy Volunteers To search for potential biomarkers of lung cancer, we systematically analyzed urinary proteins secreted from Group I lung cancer patients and healthy volunteers. First, the protein expression pattern of pooled urine samples from healthy controls (N) and lung cancer patients (L) were separated from 2DE analysis with a narrow pH range of 4-7 (FIG. 1A). One of the differentially expressed proteins was identified as GM2AP, which was marked in the 2-DE map by circles.

Figure 1B:
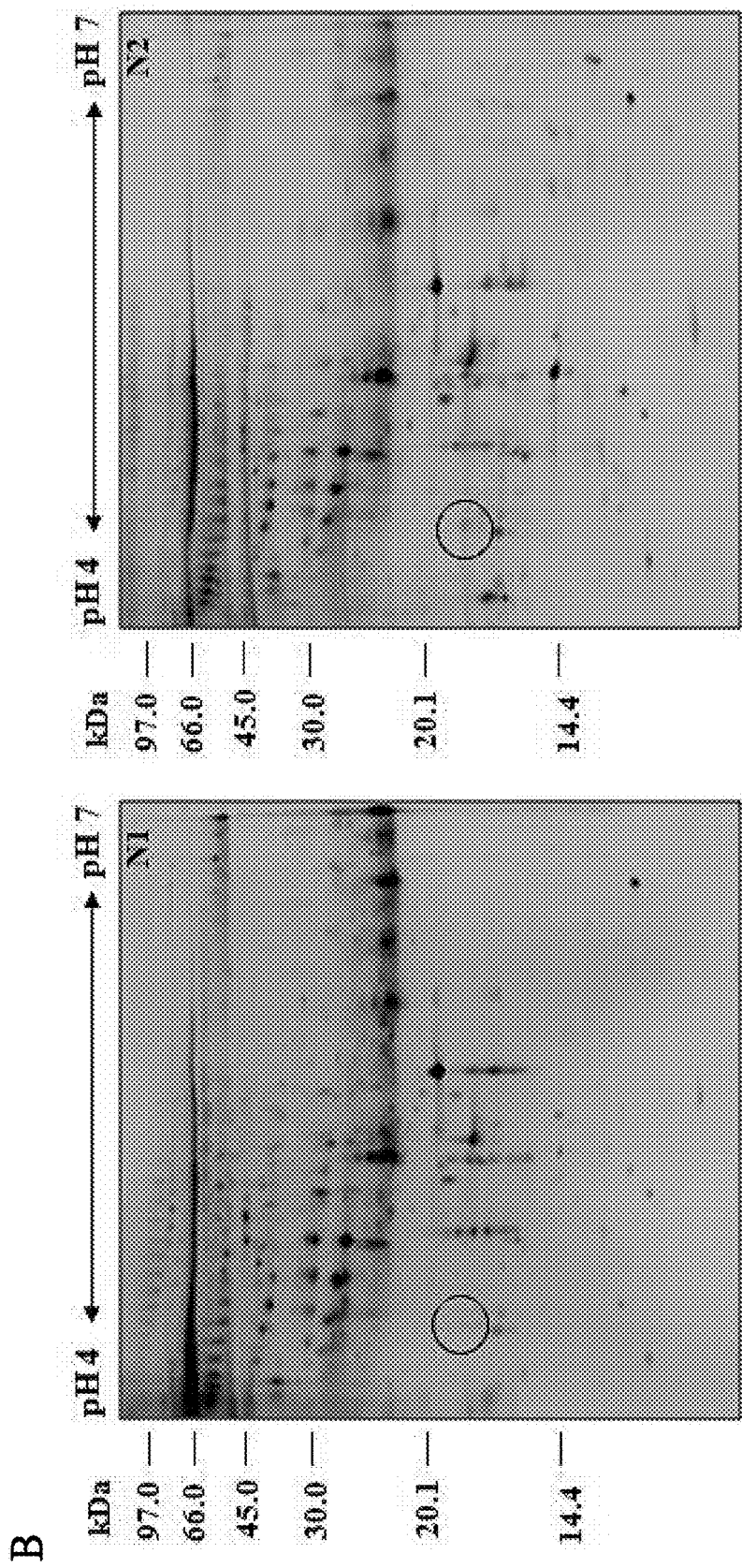
FIG. 1(B) represents the 2-DE analysis images of urine samples of healthy volunteers (N1-N4) and patients with different subtypes of lung cancer (L1: adenocarcinoma, L2: small cell lung cancer, L3: squamous cell carcioma, L4: other types of carcinoma).
Figure 1B:
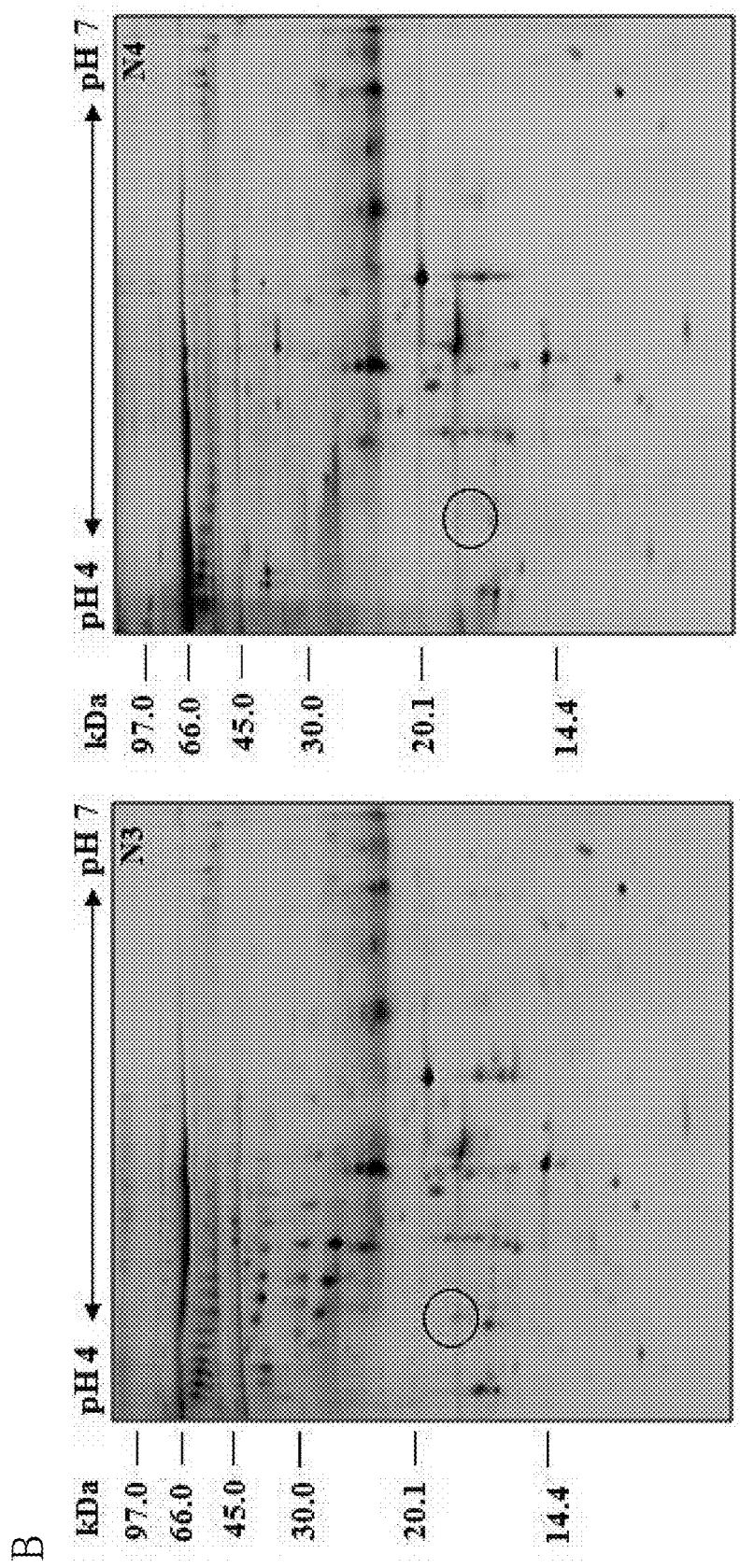
Figure 1B:
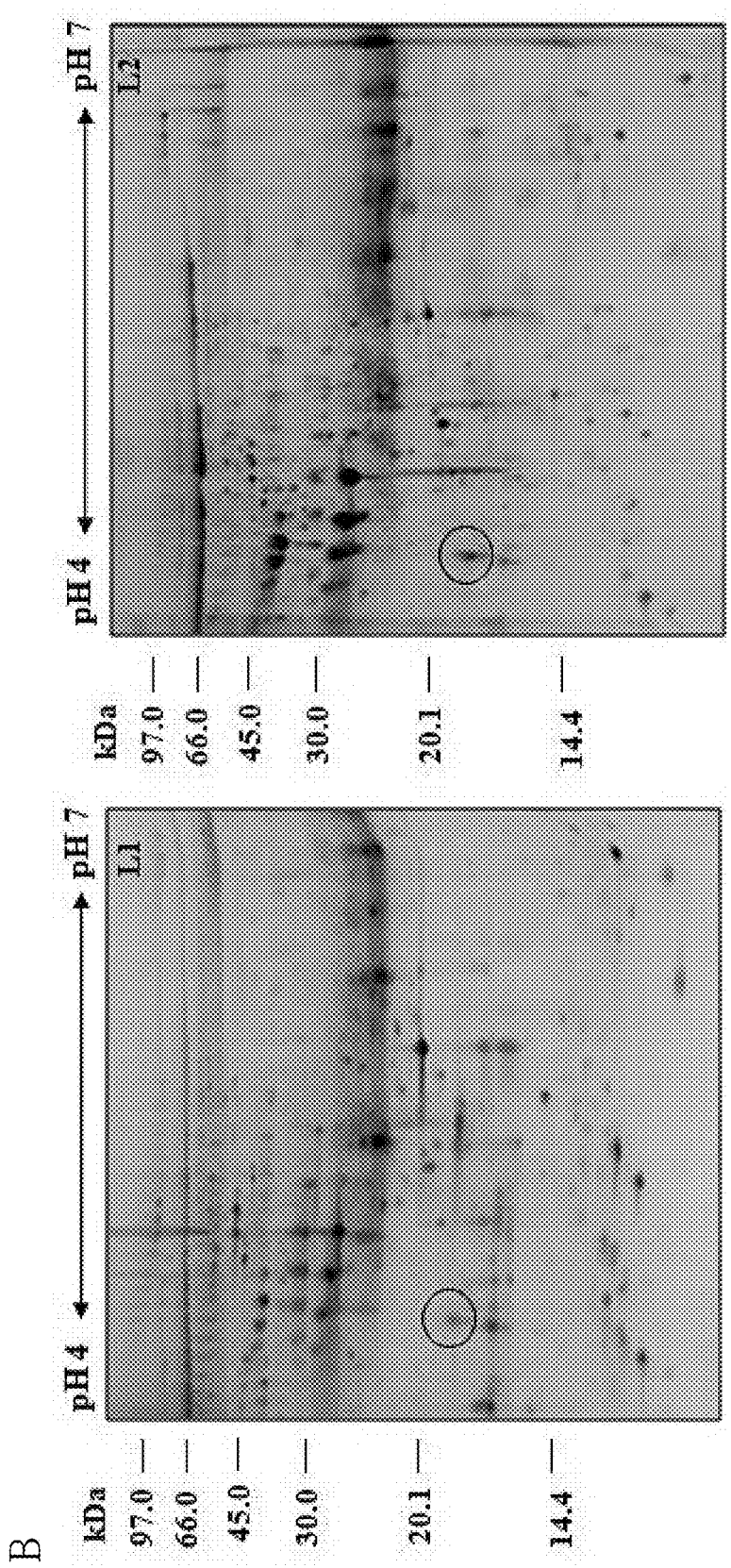
Figure 1B:
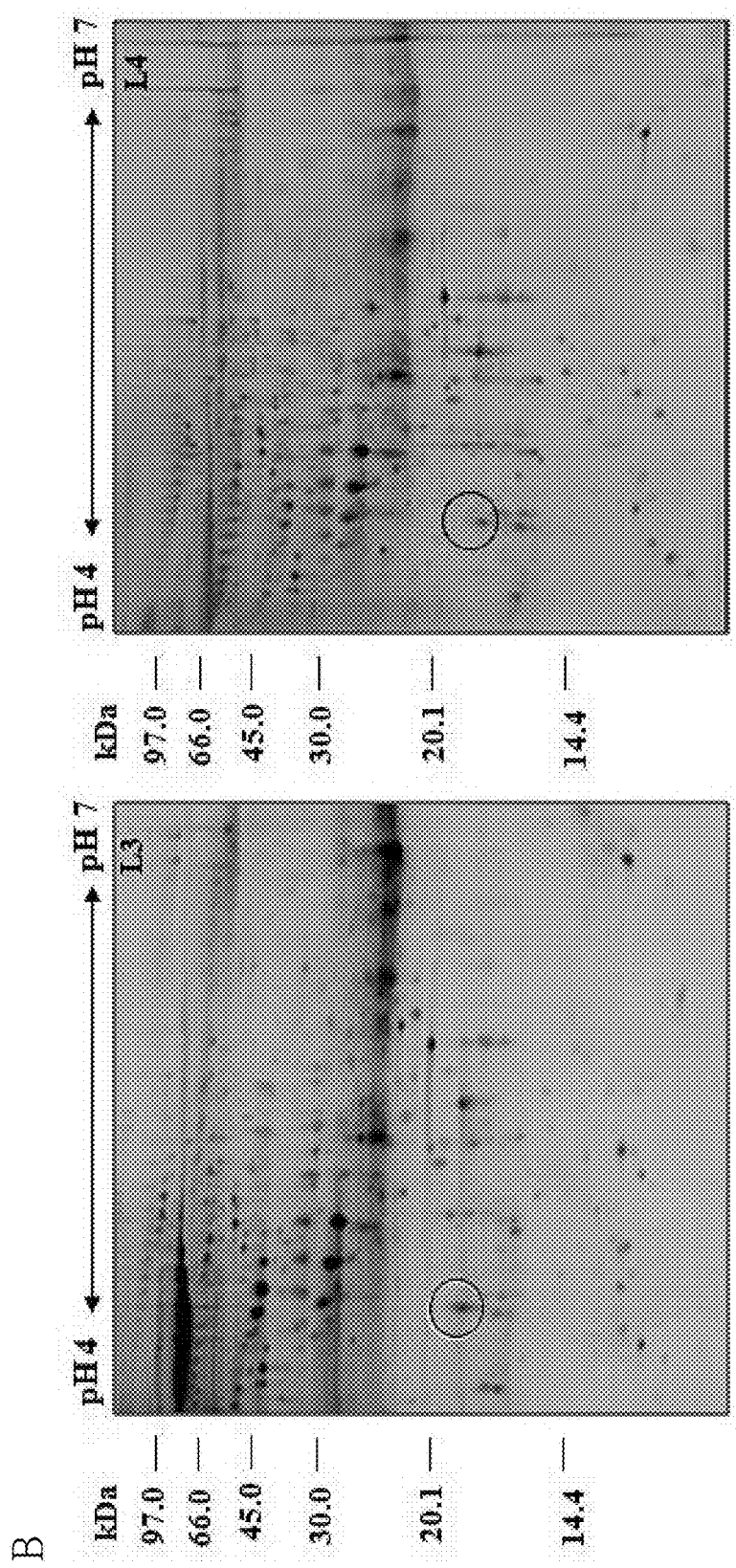

The urine samples from healthy individuals (N1-N4) and patients with different subtypes of lung cancer (L1: adenocarcinoma, L2: small cell lung cancer, L3: squamous cell carcinoma, L4: other types of carcinoma) were used for 2-DE analysis to confirm the GM2AP expression. The result revealed that GM2AP level in each subtype of lung cancer patients was greatly over-expressed compared to the mean level of healthy controls (FIG. 1B). This spot was excised from 2-DE gel and subjected to in-gel enzymatic digestion, followed by the nanoLC-MS/MS analysis. The database searches were performed against Swiss-Prot database using Mascot software, and the data was calibrated based on carbamidomethylated cysteine modification and methionine oxidation. This protein spot was identified as GM2AP (data not shown).

Example 2

Identification of GM2AP as a Lung Cancer Biomarker

To verify the cancer selective character of candidate proteins identified by mass spectrometry, the antibody-binding capacity of spot corresponding to GM2AP protein of Group I lung cancer patients and healthy control was investigated by 2-DE Western blotting to confirm the identity of the protein spot matched after 2-DE using antibodies GM2AP (data not shown). Data suggested that GM2AP was over-expressed in lung cancer patients, consistent with the result of Example 1.

In addition, the expression level of GM2AP in urine samples from Group I lung cancer patients (n=48) were validated by Western blotting analysis to compare their GM2AP levels with those from healthy controls (n=44).

Figure 2:
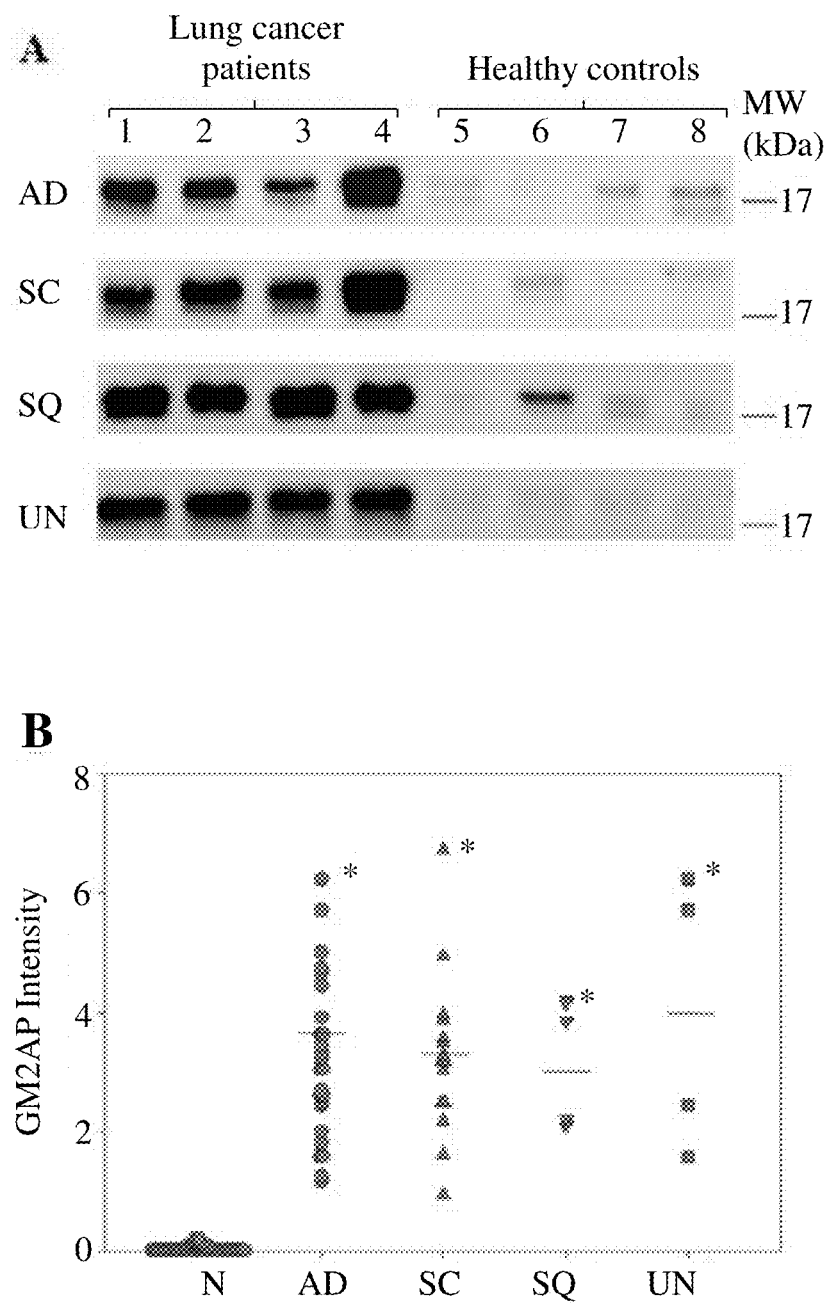
FIG. 2 represents the quantification of GM2AP levels in urine samples from Group I lung cancer patients and healthy volunteers by Western blotting. (A) Western blotting analyses of lung cancer patients suffer from adenocarcinoma (AD), small cell lung cancer (SC), squamous cell carcinoma (SQ) and other types of carcinoma (UN) and healthy volunteers. (B) Scatter plot of the quantified data from (A).

FIG. 2A represents the urinary GM2AP profiles from the four subtypes of lung cancer patients (AD: adenocarcinoma, SC: small cell lung cancer, SQ: squamous cell carcinoma, UN: other types of carcinoma) and healthy controls. The level of GM2AP was significantly increased in the each subtype of lung cancer patients when compared to the mean level of healthy controls (FIG. 2B, P<0.05). This is also consistent with the above-mentioned results.

Figure 3:
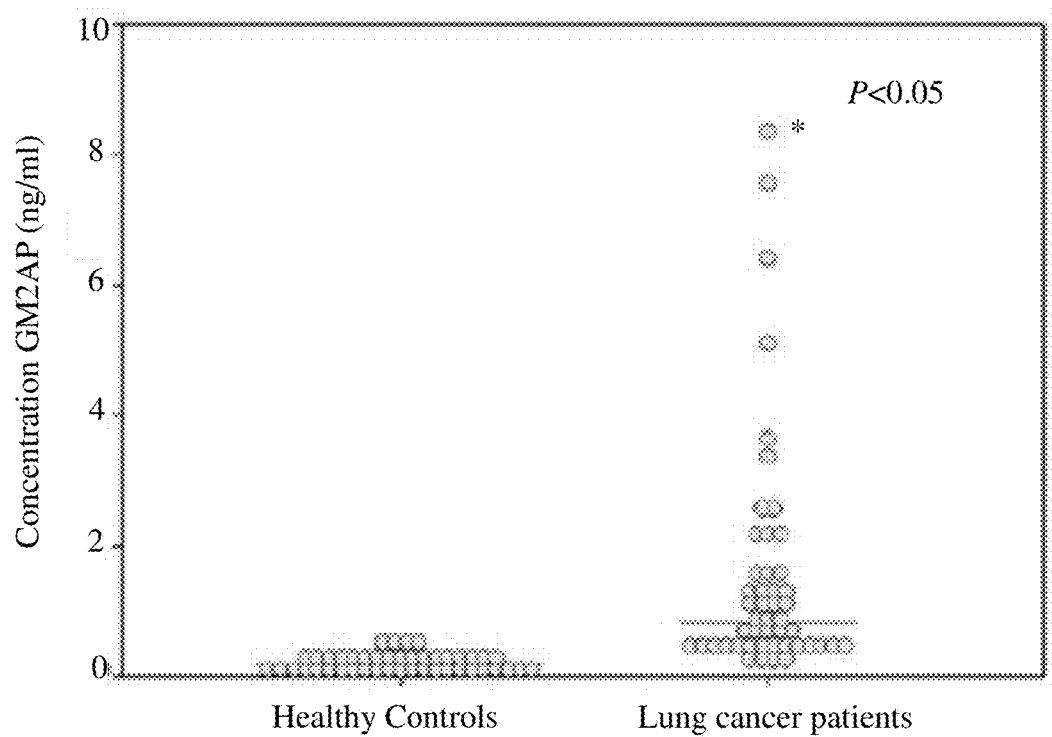
FIG. 3 represents the quantification of GM2AP levels in urine samples from Group I lung cancer patients and healthy controls by ELISA.

Western blot is a semi-quantitative method, hence ELISA was further used to quantify the expression level of GM2AP in urine of Group I lung cancer patients (n=48) and healthy controls (n=44). The mean level of GM2AP in all of lung cancer patients were measured as 1.60±1.21 ng/mL, whereas the mean level of GM2AP for healthy controls was 0.21±0.14 ng/mL. There was a significantly increase in the GM2AP level for patients compared to healthy controls (P<0.05), that is about 7.62 fold increase on the median (FIG. 3).

The urinary GM2AP level measured in the male patients (1.16±1.07 ng/mL) was higher than that measured in the female patients (1.13±1.05 ng/mL). According to histologic type, the urinary GM2AP level measured in patients with adenocarcinoma, small cell lung cancer and squamous cell carcinoma were 1.25±1.12 ng/mL, 1.48±1.35 ng/mL and 2.27±2.20 ng/mL, respectively. The urinary GM2AP level was measured as 1.69±1.54 ng/mL and 0.63±0.38 ng/mL in patients with stage III and IV, respectively. The expression levels of GM2AP of all the patients were subjected to statistical analysis, and significant correlation (P<0.05) was found between the expression levels of GM2AP in urine and histology cancer type. An overexpression of GM2AP level was observed in 54.2% of patients with adenocarcinoma, 29.2% of patients with small cell lung cancer, 8.3% of patients with squamous cell carcinoma, and 8.3% of patients with other carcinoma. The data of Table 1 also showed that the urinary GM2AP level was significantly higher in patients with squamous cell carcinoma than in those with adenocarcinoma and small cell lung cancer, whereas age, gender and pathologic stage were determined as not correlated with the urinary GM2AP level because there was no statistically significant difference (Table 1).

TABLE 1

Urinary GM2AP level of Group I lung cancer patients

|  | n | GM2AP mean ± SD (ng/mL) | P value |
|---|---|---|---|
| All patients | 48 | 1.60 ± 1.21 |  |
| Gender |  |  |  |
| Male | 33 | 1.16 ± 1.07 | 0.358 |
| Female | 15 | 1.13 ± 1.05 |  |
| Histology |  |  |  |
| Adenocarcinoma | 25 | 1.25 ± 1.22 | 0.009 |
| Small cell lung cancer | 15 | 1.48 ± 1.35 |  |
| Squamous cell carcinoma | 4 | 2.27 ± 2.20 |  |
| Other types of carcinoma | 4 | 2.99 ± 2.63 |  |
| Pathologic stage |  |  |  |
| III | 7 | 1.69 ± 1.54 | 0.312 |
| IV | 41 | 0.63 ± 0.38 |  |

Figure 4:
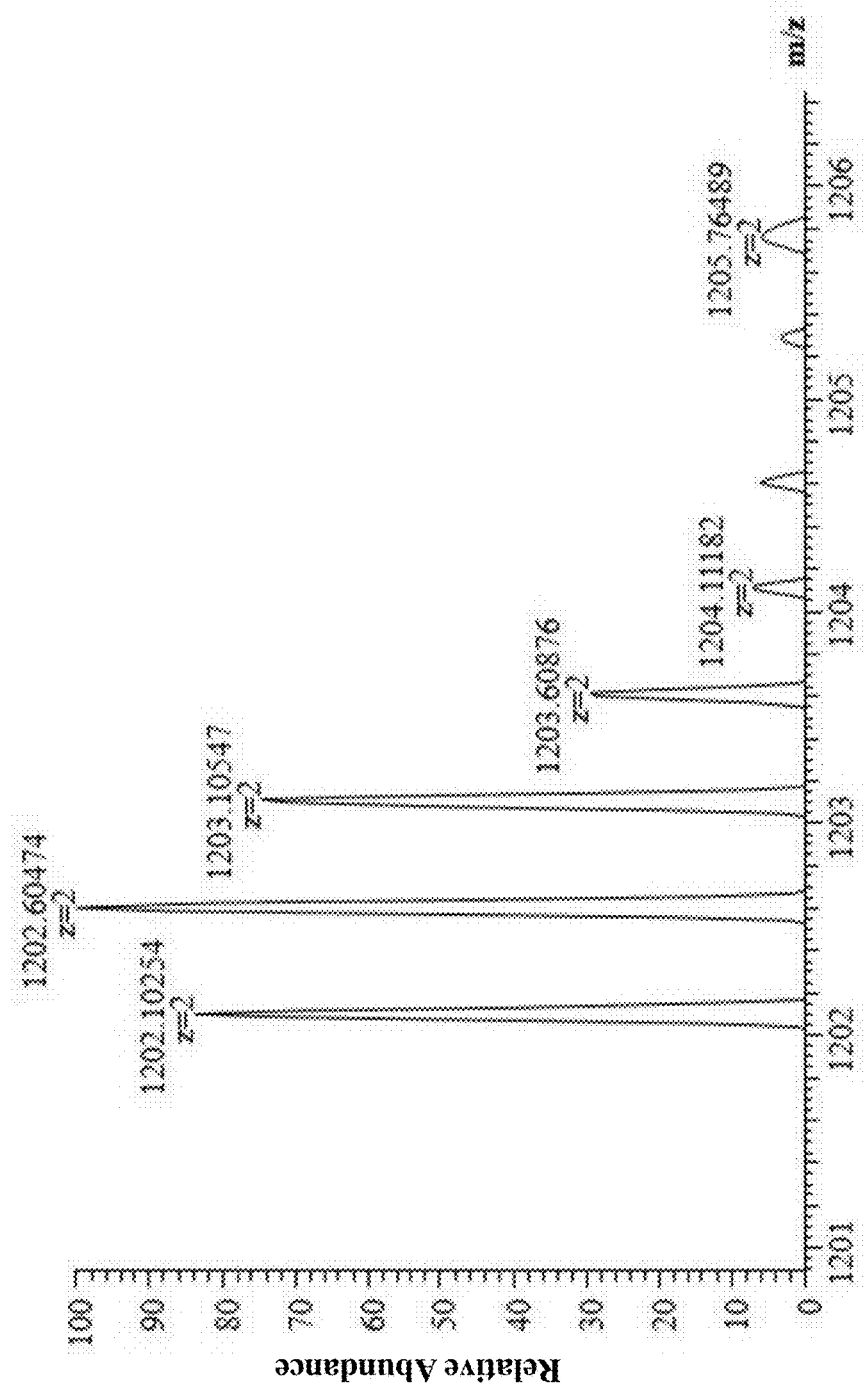
FIG. 4 represents the mass spectra of the glycopeptides of urinary GM2AP in lung cancer patient.
Figure 4:
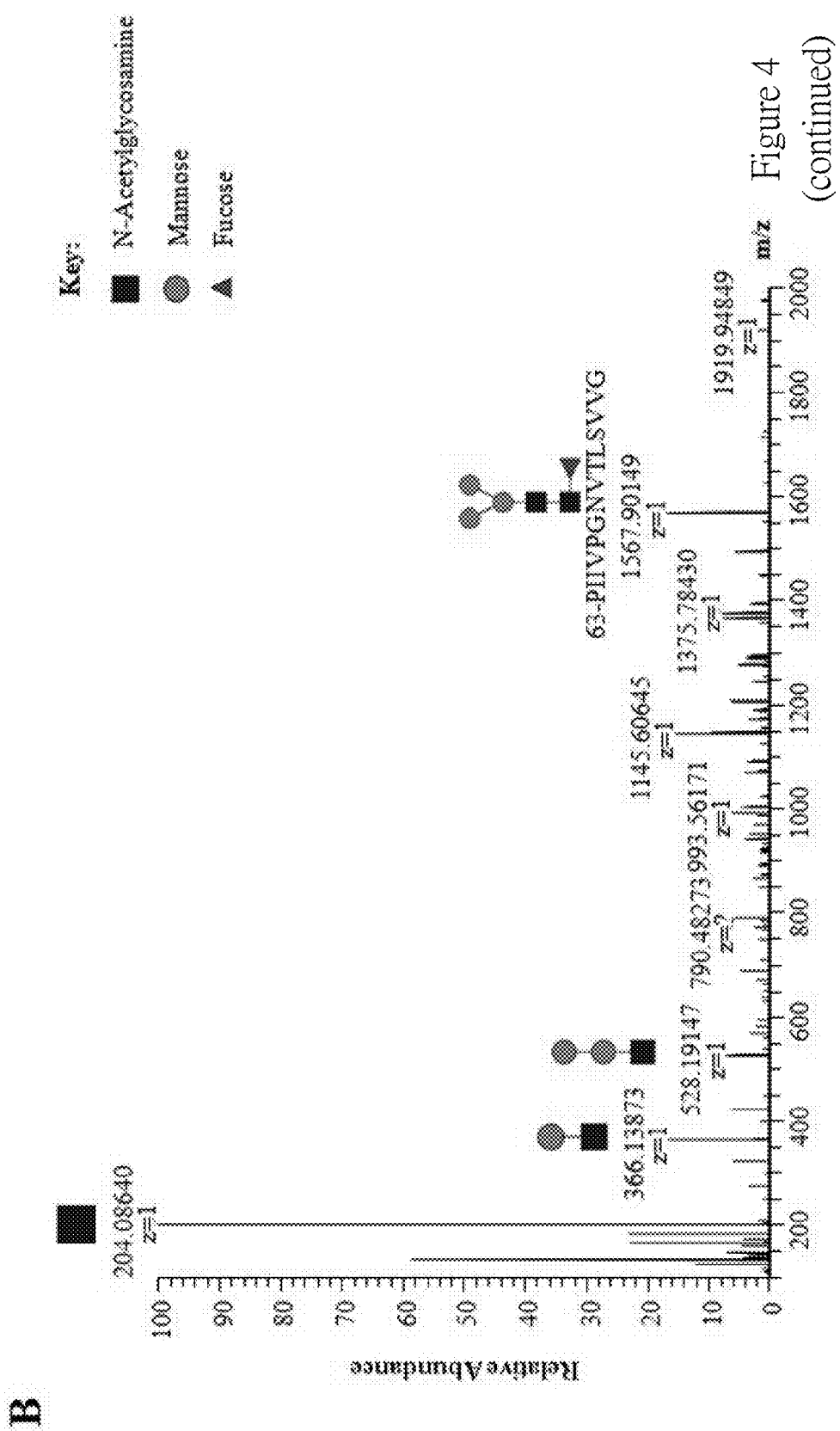

GM2AP is a glycoprotein that was significantly increased in urine of lung cancer patients. The glycosylation change in the glycan moieties of glycoproteins may provides opportunities to discover new biomarkers[23] or improve on the specificity of existing cancer biomarkers.[24,25] However, the glycan structure of urinary GM2AP in lung cancer patients has not been reported. In this invention, we firstly used MALDI-TOF/MS analysis to confirm the intact protein mass of GM2AP in urine samples from lung cancer patients. The molecular mass of GM2AP was higher than that of the predicted protein mass, and this is a characteristic of glycosylation modification. N-linked glycosylation is the most common form of glycosylation found in eukaryotes. It is occurs when glycans are attached to asparagine residues (Asn) on the core protein. Therefore, the N-linked glycan structure of urinary GM2AP from lung cancer patients was determined using nanoLC-MS/MS analysis. The glycopeptides ions of GM2AP can be fragmented efficiently by the HCD feature of a linear LTQ Orbitrap hybrid mass spectrometer. An attractive aspect of this dissociation option is the generation of distinct $Y_1$ ions (peptide plus one HexNAc), thus allowing unequivocal assignment of N-glycosylation sites of glycoproteins. As a result, the common glycan oxonium ions and the $Y_1$ ion could be detected. We found that the N-glycan structure of GM2AP was corresponding to the structure of $(Hex)_3(HexNAc)_2(Fuc)_1$ linked with the peptide (PIVVPGNVTLSVVG) (SEQ ID No. 3) comprised in GM2AP protein (FIG. 4). In general, N-glycosylated proteins comprise a conserved core structure consisting of two N-acetylglycosamine residues, which is linked to asparagine followed by three branched mannosyl residues.[7] In the N-linked glycan structure of GM2AP from lung cancer patients, it was found a fucose residue was attached on the common core protein. This fucose residue was confirmed on the 2-DE Western blotting and followed by AAL lectin staining because the commercially available AAL lectin makes the fucose preferentially linked to acetylglycosamine present on glycoprotein through (α-1,6) or (α-1,3) linkage. The AAL lectin signal of lung cancer patient was stronger than that of compared to healthy control, which showed increased fucosylated GM2AP (data not shown). However, the glycan structure of urinary GM2AP of healthy control was not detected. This is because the concentration of GM2AP was too low and some healthy donors did not excrete this protein into their urine. Some reports suggest that structural changes in cell surface carbohydrates may promote tumor transformation.[23,26] Therefore, our findings suggest that the GM2AP may be useful as a potential urinary marker to monitor lung cancer progression.

Example 3

Figure 5:
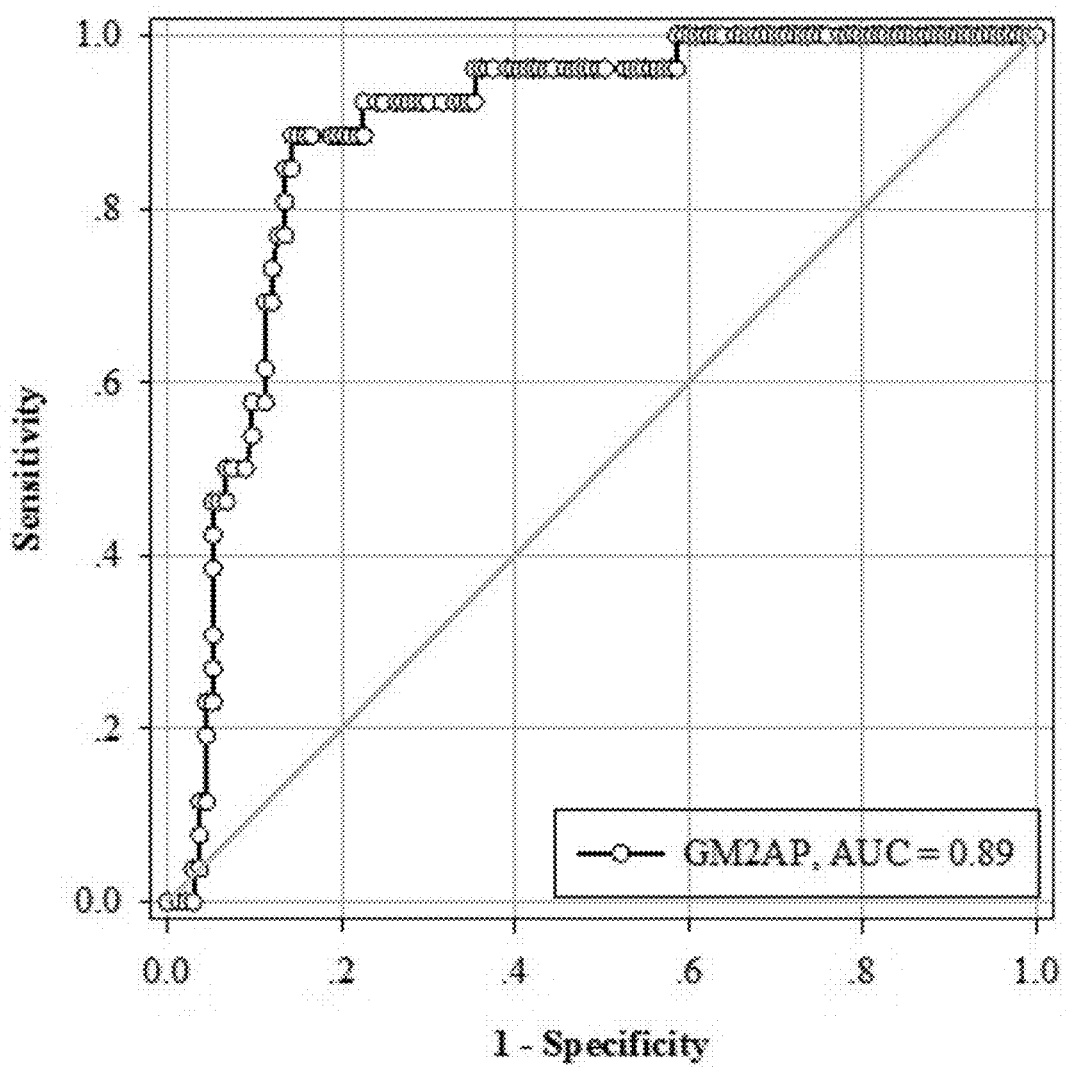
FIG. 5 represents GM2AP level in urine and serum samples from Group II lung cancer patients and healthy volunteers: (A) the ROC curve of the urine samples; (B) the dot histogram plot demonstrated the distribution of GM2AP levels in urine samples; (C) the ROC curve of the serum samples; (D) the dot histogram plot demonstrated distribution of GM2AP levels in serum samples.
Figure 5:
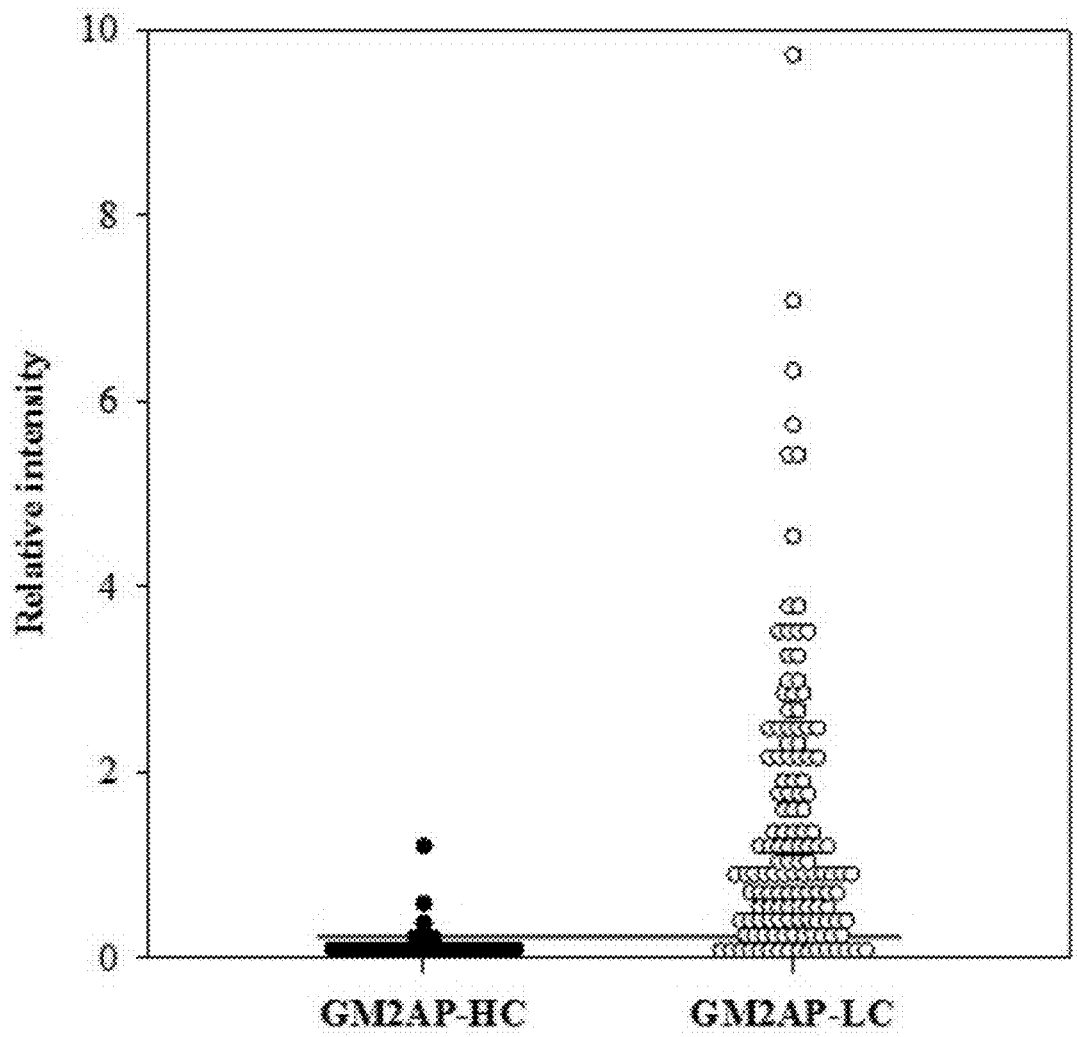
Figure 5:
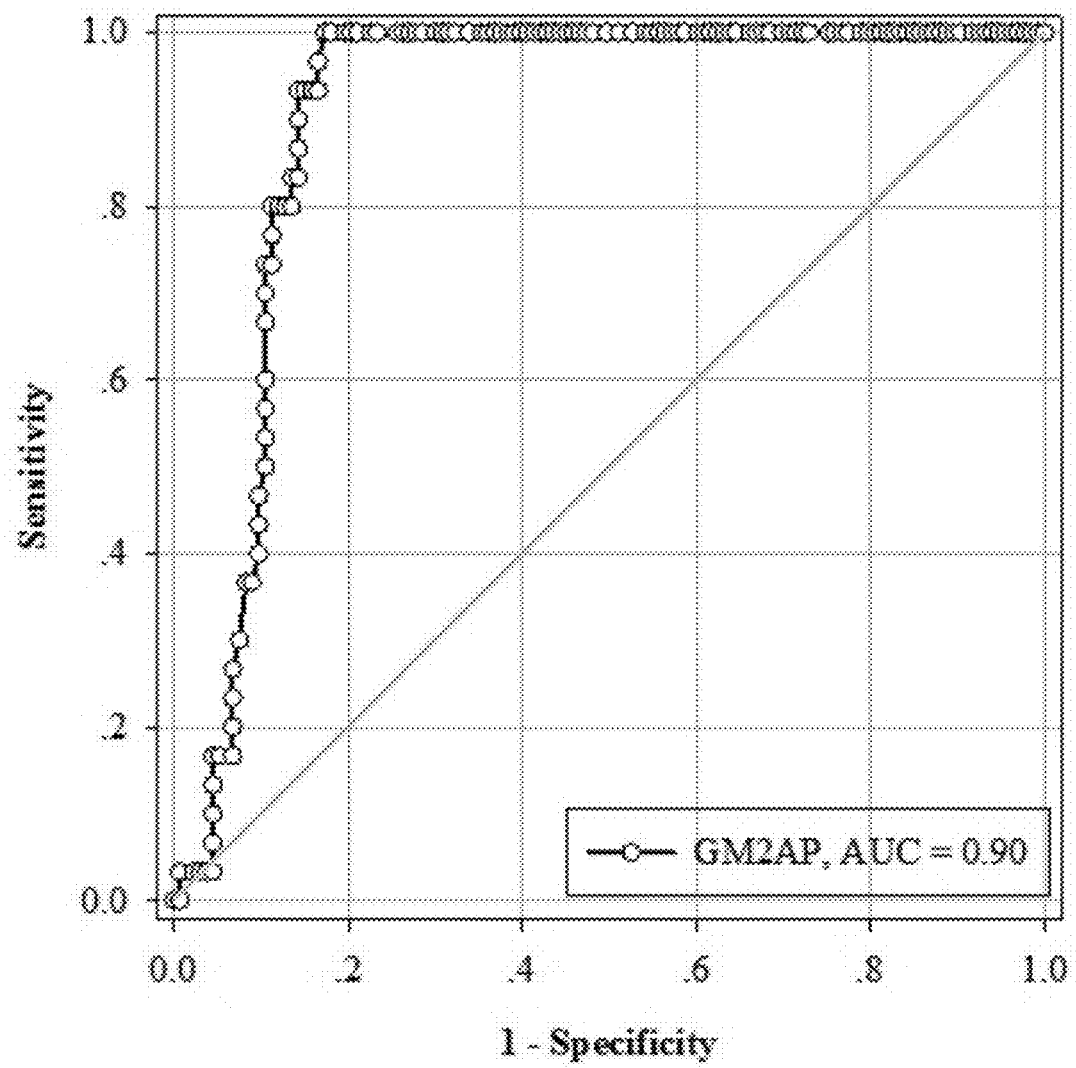
Figure 5:
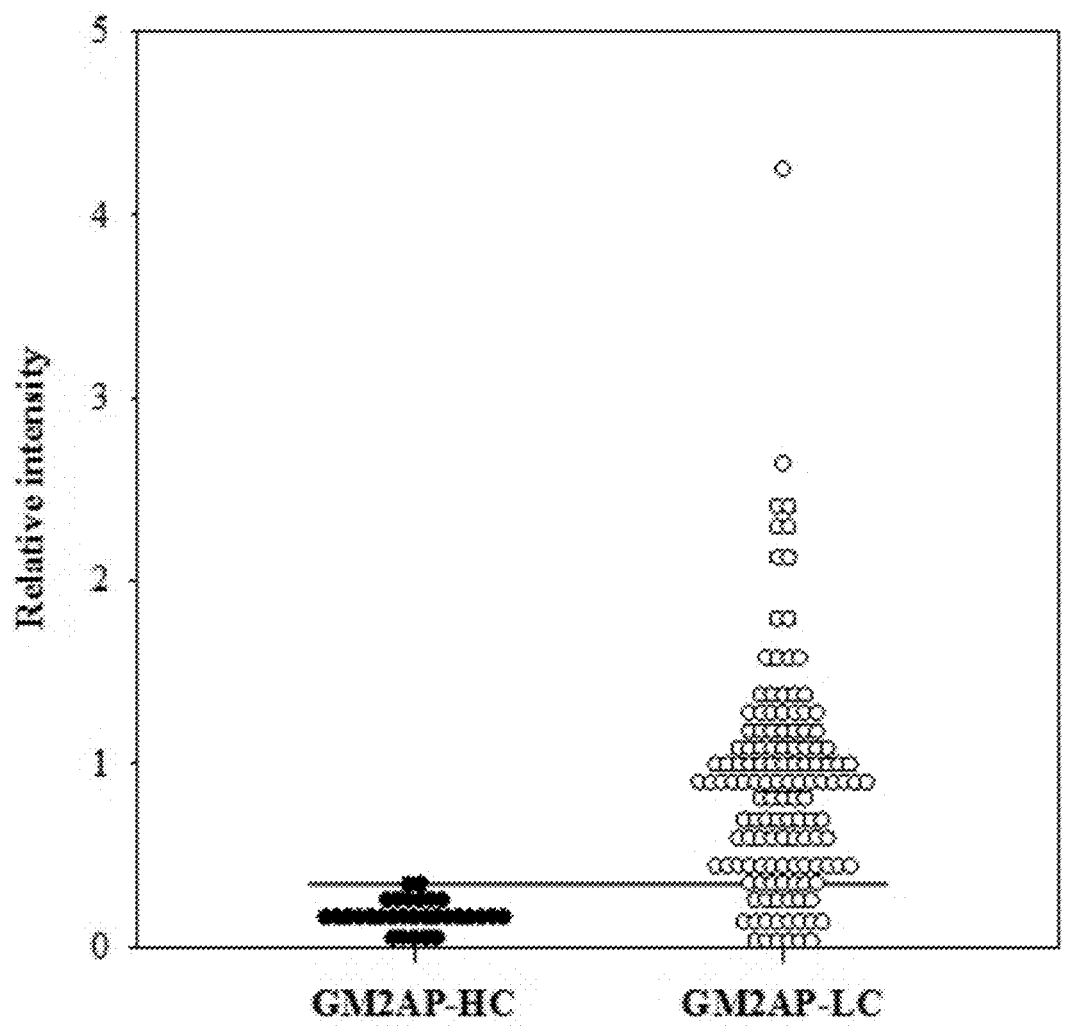

Expression of GM2AP Level in Urine and Serum Samples of Patients with Lung Cancer Patients and Healthy Volunteers First, urine and serum samples of the Group II lung cancer patients were examined by Western blotting, using those from healthy volunteers as controls. The result showed that GM2AP levels in urine and serum samples were greatly increased in patients when compared to those from healthy volunteers. ELISA assay was employed to quantify the GM2AP levels in urine and serum samples from lung cancer patients and healthy volunteers. The mean urinary GM2AP level in all lung cancer patients was 1.46±1.38 ng/mL whereas the mean GM2AP level in healthy volunteers was 0.18±0.13 ng/mL. There was an 8.03±1.50 folds increase of GM2AP level in urine compared to those obtained from healthy volunteers, which is similar to the result obtained from Group I. ROC curve analysis showed that the urinary GM2AP level could be used to predict the diagnosis of lung cancer with an AUC of 0.890 (95% CI, 0.83-0.95) at a cut-off point of 0.234. This cut-off point provides 88.46% sensitivity and 85.71% specificity, as shown in FIG. 5A. A dot histogram plot demonstrates the distribution of GM2AP levels in urines of healthy volunteers (FIG. 5B).

The mean serum GM2AP level in lung cancer patients was calculated as 0.92±0.27 ng/mL whereas the mean of GM2AP level in healthy volunteers was calculated as 0.17±0.07 ng/mL. There was a 5.41±0.73 folds increase in the serum compared to those obtained from healthy volunteers. The ROC curve showed an AUC of 0.90 (95% CI, 0.85-0.95) at a cut-off point of 0.342, with 100% sensitivity and 82.71% specificity in predicting lung cancer (FIG. 5C). FIG. 5D demonstrates the distribution of GM2AP levels in serum of healthy volunteers.

The area under ROC curves suggested a significant increase of GM2AP levels in urine and serum in lung cancer patients ($P<0.0001$), and it demonstrates a high accuracy as a potential diagnostic marker for lung cancer.

Example 4

Correlation Between the Expression of GM2AP in Urine and Serum from Lung Cancers Patients and Clinicopathological Features The GM2AP levels in urine and serum samples determined by ELISA were correlated with the clinicopathological features of lung cancer patients. The urinary GM2AP levels in adenocarcinoma, small cell lung cancer, squamous cell carcinoma and other types of carcinoma were 1.97±1.45 ng/mL, 1.09±0.85 ng/mL, 0.57±0.48 ng/mL and 2.42±2.02 ng/mL, respectively. The urinary GM2AP levels in stage I, II, III and IV were 2.31±1.39 ng/mL, 2.53±1.65 ng/mL, 1.57±1.40 ng/mL and 1.17±1.02 ng/mL, respectively (Table 2). In addition, the serum GM2AP levels in adenocarcinoma, small cell lung cancer, squamous cell carcinoma and other types of carcinoma were at 0.89±0.63 ng/mL, 0.78±0.63 ng/mL, 1.10±0.21 ng/mL and 0.78±0.33 ng/mL, respectively. The serum GM2AP level was also measured to be 1.61±0.93 ng/mL, 0.71±0.29 ng/mL, 0.98±0.52 ng/mL and 0.71±0.43 ng/mL in patients with stage I, II, III and IV, respectively (Table 2). The mean urinary GM2AP level was significantly higher than that in serum ($P=0.0003$). There was a significant difference in the expression of urinary GM2AP level among histology subtypes ($P=0.049$) and pathology stages ($P=0.009$), while the expression of serum GM2AP level only significantly differed in pathology stages ($P<0.0001$). There was no significant difference between GM2AP expression and age or gender. The data of Group I and Group II shows some difference in the squamous cell carcinoma patients, which may be caused by the aetiological difference of squamous cell carcinoma occurred in different areas.

TABLE 2

Urinary and serum GM2AP level of Group II lung cancer patients

| | GM2AP (ng/mL) | | | | | |
|---|---|---|---|---|---|---|
| | Urine | | | Serum | | |
| Variable | n | mean ± SD | P value | n | mean ± SD | P value |
| All healthy volunteers | 26 | 0.18 ± 0.13 | | 30 | 0.17 ± 0.07 | |
| Gender | | | | | | |
| Male | 15 | 0.23 ± 0.19 | 0.219 | 13 | 0.19 ± 0.08 | 0.408 |
| Female | 11 | 0.11 ± 0.09 | | 17 | 0.16 ± 0.07 | |
| All patiends | 133 | 1.46 ± 1.38 | | 133 | 0.92 ± 0.27 | |
| Gender | | | | | | |
| Male | 61 | 1.45 ± 1.31 | 0.244 | 61 | 1.02 ± 0.18 | 0.354 |
| Female | 72 | 1.30 ± 1.23 | | 72 | 1.05 ± 0.35 | |
| Histology | | | | | | |
| Adenocarcinoma | 111 | 1.97 ± 1.45 | 0.049 | 111 | 0.89 ± 0.63 | 0.794 |
| Small cell lung cancer | 4 | 1.09 ± 0.85 | | 4 | 0.78 ± 0.63 | |
| Squamous cell carcioma | 11 | 0.57 ± 0.48 | | 11 | 1.10 ± 0.21 | |
| Other types of carcinoma | 7 | 2.42 ± 2.02 | | 7 | 0.78 ± 0.33 | |
| Pathologic stage | | | | | | |
| I | 18 | 2.31 ± 1.39 | 0.009 | 18 | 1.61 ± 0.93 | <0.0001 |
| II | 6 | 2.53 ± 1.65 | | 6 | 0.71 ± 0.29 | |
| III | 25 | 1.57 ± 1.40 | | 25 | 0.98 ± 0.52 | |
| IV | 84 | 1.17 ± 1.02 | | 84 | 0.71 ± 0.43 | |

Example 5

Figure 6:
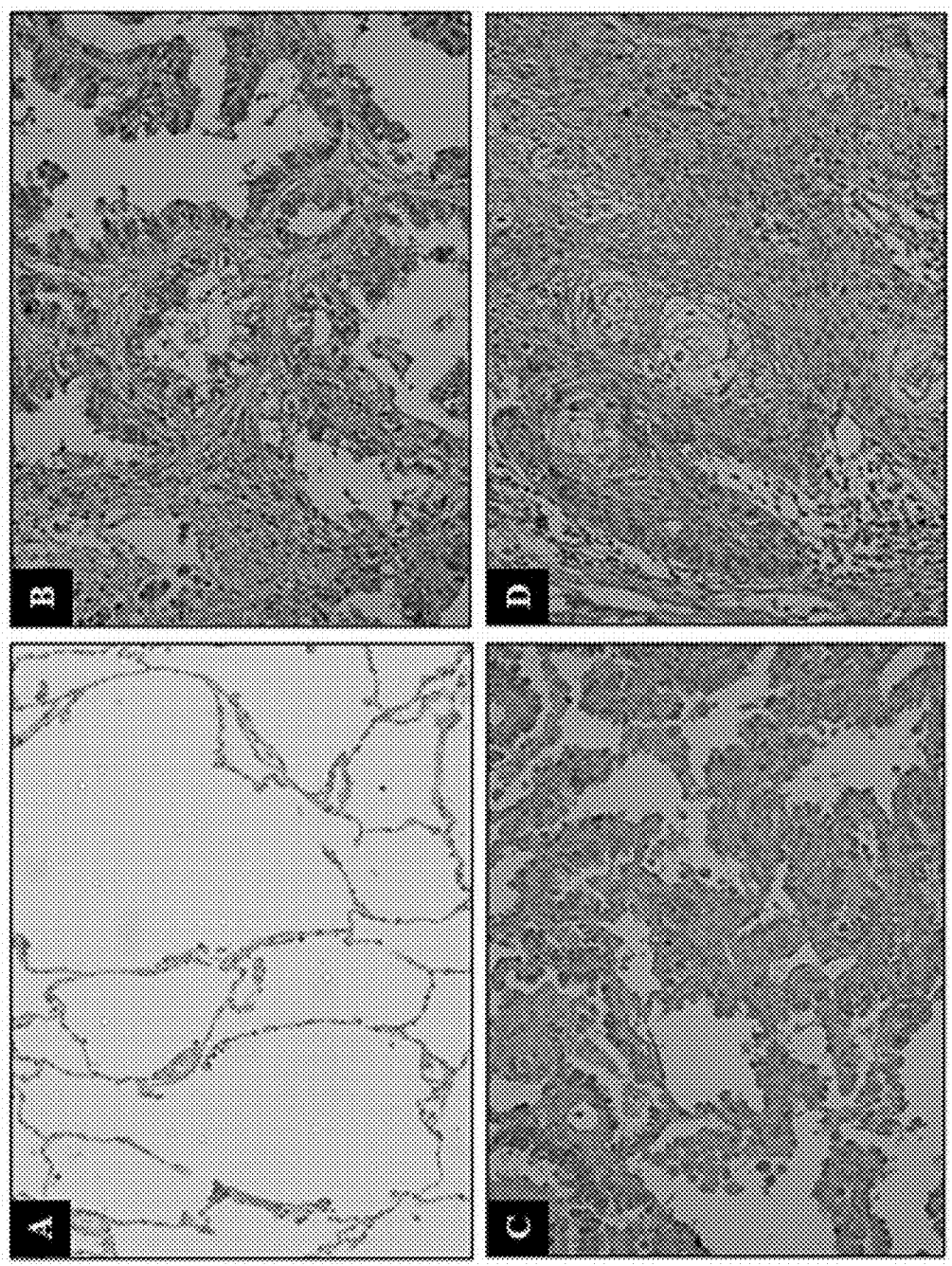
FIG. 6 represents the IHC staining of lung tissue from NSCLC patients: (A) non-tumor lung tissue; (B) invasive adenocarcinoma (GM2AP positive); (C) adenocarcinoma in situ (GM2AP positive); and (D) squamous cell carcinoma (GM2AP positive). Magnification: ×200.

Correlation Between the Expression of GM2AP in NSCLC Tissues and Clinicopathological Feathers The number of NSCLC patients is more than small cell lung cancer patients. Therefore, the pathologic tissue specimens from 143 NSCLC patients from Department of Pathology, National Taiwan University Hospital were subsequently detected by IHC staining. The expression of GM2AP was detectable in lung tissue samples from 122 NSCLC patients (including 90 of 106 invasive adenocarcinoma patients, 22 of 26 squamous cell carcinoma patients and 10 of 11 adenocarcinoma in situ (previously named as bronchioloalveolar carcinoma) patients), which makes a 83.9% positive rate of tissue expression of GM2AP in NSCLC and brown granules were observed in the cytoplasm via staining (FIG. 6). The distribution of IHC score was 21 in score 0, 92 in score 1 and 30 in score 2.

There is no difference among different histology subtypes in GM2AP expression. But there is a significant correlation between GM2AP expression and pathologic stages ($P=0.001$). The positive rate of GM2AP was 75.0% (45 out of 60) in stage I, 95.1% (58 out of 61) in stage II and 95.0% (19/20) in stage III, but 0% in stage IV (0 out of 2). There were no statistical correlations between GM2AP expression and the remaining clinicopathologic features, such as age and gender (Table 3).

TABLE 3

GM2AP expression in NSCLC tissue

| IHC score | GM2AP expression | | | P value |
|---|---|---|---|---|
| | 0 (n = 21) | 1 (n = 92) | 2 (n = 30) | |
| Age | | | | |
| Median (range) | 64 (38-76) | 64 (33-81) | 68 (41-82) | 0.425 |
| Gender | | | | |
| Male | 11 | 52 | 16 | 0.916 |
| Female | 10 | 40 | 14 | |
| Histology type | | | | |
| Adenocarcinoma | 16 | 72 | 18 | 0.234 |
| Squamous cell carcinoma | 4 | 15 | 7 | |
| Adenocarcinoma in situ | 1 | 5 | 3 | |
| Pathologic stage | | | | |
| I | 15 | 30 | 15 | 0.001 |
| II | 3 | 48 | 10 | |
| III | 1 | 14 | 5 | |
| IV | 2 | 0 | 0 | |

Example 6

Association Between Expression of GM2AP in NSCLC Tissues and Survival

Figure 7:
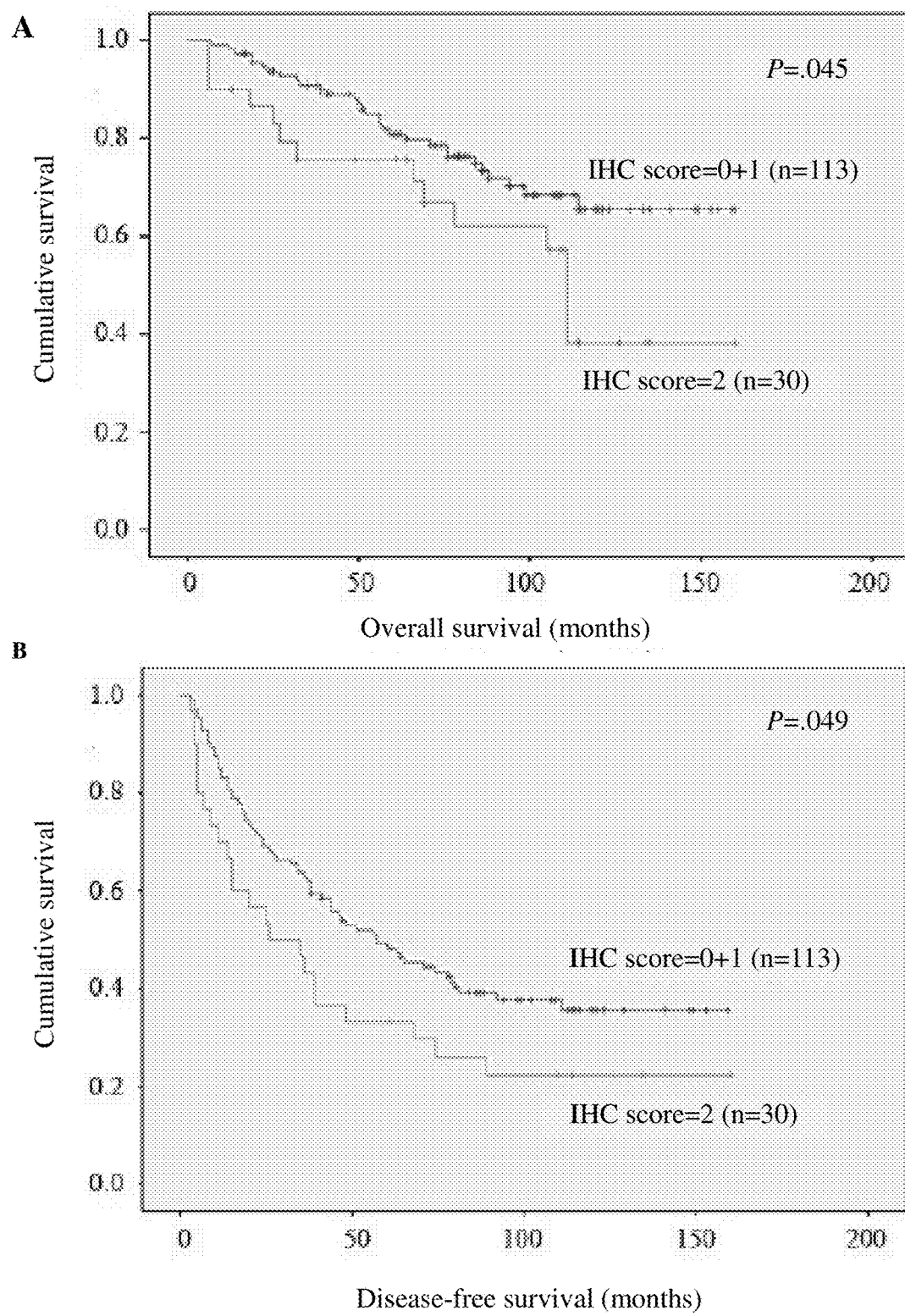
FIG. 7 represents the Kaplan-Meier analysis of lung tissue from NSCLC patients: (A) the relationship between GM2AP expression and overall survival; and (B) the relationship between GM2AP expression and disease-free survival.

The association between tissue GM2AP expression in NSCLC and the survival of 143 NSCLC patients was analyzed with Kaplan-Meier survival analysis. Patients with a high GM2AP expression (score 2) were likely to have a significantly shorter overall survival (P=0.045) (FIG. 7A) and disease-free survival (P=0.049) (FIG. 7B). Since GM2AP expression was significantly correlated with pathologic stage, we further determined the impact of GM2AP IHC score and pathology stage on the survival of NSCLC patients. The multivariate analysis of disease-free survival revealed that in addition to the pathologic stage (stage I/II vs III/IV; odds ratio [OR] 0.335 [95% CI, 0.163-0.689]; P=0.003), the IHC score (0/1 vs 2; OR 0.475 [95% CI, 0.250-0.906]; P=0.024) was also an independent predictor of disease recurrence (Table 4). Similar results were also shown in overall survival, in which the pathologic stage; I/II vs III/IV (OR 0.364 [95% CI, 0.216-0.612]; P<0.001) and the IHC score; 0/1 vs 2 (OR 0.563 [95% CI, 0.349-0.910]; P=0.019) was both independent predictors (Table 4).

TABLE 4

Multivariate analysis of the GM2AP expression in overall survival and disease-free survival in NSCLC patients

| Variable | Hazard ratio (98% CI) | P value |
|---|---|---|
| Overall survival | | |
| Stage I/II vs Stage III/IV | 0.364 (0.216-0.612) | <0.001 |
| IHC score 0/1 vs 2 | 0.563 (0.349-0.910) | 0.019 |
| Disease-free survival | | |
| Stage I/II vs Stage III/IV | 0.335 (0.163-0.689) | 0.003 |
| IHCscore 0/1 vs 2 | 0.475 (0.250-0.906) | 0.024 |

Despite tremendous works endeavored in seeking for specific cancer markers, very few have become clinically applicable, such as PSA in prostate cancer[27] and CA-125 in gynecological oncology.[28,29] In this invention, we found that the expression of GM2AP in both urine and serum are significantly correlated with pathologic stage. In earlier stages of lung cancer, the levels of GM2AP tend to be higher.

Using IHC, we also demonstrated that GM2AP was expressed essentially by tumor cells, but none of the surrounding non-tumor tissue expressed GM2AP. Except pathology stages, there was no correlation between the GM2AP expression and histology type, age and gender. The IHC score of GM2AP expression in stage I, II and III was higher, but it is much lower in stage IV (2 cases). Our results suggest that urinary and serum GM2AP levels can be potential markers for assisting lung cancer diagnosis, especially for early lung cancer. The aberrant expression of GM2AP is related to tumor associated gangliosides involving in cancer progression and plays a role in the induction of invasion and metastasis.[16] Antitumor immune response was suppressed by gangliosides synthesized by tumor cells and shed into their microenvironment.[27-32] Many studies have shown that tumor-derived gangliosides inhibit the cellular immune response in vitro, such as natural killer cell cytotoxicity.[33-35] Recent study showed that GM2AP impairs insulin signaling.[36] It is possible that GM2AP may inhibit insulin signaling to reduce uptake glucose in normal cell, therefore, cancer cell will have more glucose to support cell growth. On the other hand, GM2AP can hydrolyze platelet activating factor (PAF) and inhibit PAF-initiation inflammation response,[37] hence, GM2AP may help cancer cell to escape from antitumor response by inhibiting inflammation. Because GM2AP expression at stage III and IV was lower than I and II, the anti-inflammatory property of GM2AP may play an important role in early stage of cancer through reducing immune response that recognizes or destroys tumor cells.

Besides being a diagnostic marker, GM2AP can also be a prognostic marker. The higher expression of GM2AP (IHC score 2) predicted shorter overall survival and disease-free survival. The results of multivariate analysis suggested that GM2AP score is an independent prognostic factor besides pathology stage. The results indicated that GM2AP could possibly induce tumor growth. A higher expression of GM2AP in early stages of lung cancer may imply early metastatic disease. This finding supported that GM2AP may be a pivotal modulator involved in cancer development.

In summary, the present invention demonstrates that the level of the specific glycosylated GM2AP present in urines is higher in lung cancer patients and proposed a remarkable involvement of GM2AP in the development of lung cancer. The level of GM2AP present in urines and sera can be useful for the auxiliary diagnosis of lung cancer. The expression of GM2AP in lung cancer tissues could be a good prognostic factor for NSCLC, especially in early stage, in predicting both overall survival and disease-free survival. This protein has a great potential to serve as both diagnostic and prognostic marker for lung cancer.

REFERENCES

1. Siegel R, Naishadham D, Jemal A. Cancer statistics, 2013. *CA Cancer J Clin* 2013; 63:11-30.
2. Molina J R, Yang P, Cassivi S D, et al. Non-small cell lung cancer: epidemiology, risk factors, treatment, and survivorship. *Mayo Clin Proc* 2008; 83:584-594.

3. Mulshine J L. Current issues in lung cancer screening. *Oncology* 2005; 19:1724-1730; discussion 30-1.
4. Mountain C F. Revisions in the international system for staging lung cancer. *Chest* 1997; 111:1710-1717.
5. Tantipaiboonwong P, Sinchaikul S, Sriyam S, et al. Different techniques for urinary protein analysis of normal and lung cancer patients. *Proteomics* 2005; 5:1140-1149.
6. Potprommanee L, Ma H T, Chen C H, et al. Human urinary GM2-activator protein as a potential biomarker for lung cancer. *J Proteomics Bioinform* 2013; 6:264-270.
7. Kornfeld R, Kornfeld S (1985) Assembly of asparagine-linked oligosaccharides. Annu Rev Biochem 54: 631-664.
8. Hirst W, Schubert J, Machleidt W, et al. The complete amino-acid sequences of human ganglioside GM2 activator protein and cerebroside sulfate activator protein. *Eur J Biochem* 1990; 192:709-714.
9. Wright C S, Li S C, Rastinejad F (2000) Crystal structure of human GM2-activator protein with a novel beta-cup topology. J Mol Biol 304: 411-422.
10. Rigat B, Wang W, Leung A, et al. Two mechanisms for the recapture of extracellular GM2 activator protein: evidence for a major secretory form of the protein. *Biochemistry* 1997; 36:8325-8331.
11. Sandhoff K, Kolter T. Topology of glycosphingolipid degradation. *Trends Cell Biol* 1996; 6:98-103.
12. Hirst W, Sandhoff K. Activator proteins and topology of lysosomal sphingolipid catabolism. *Biochim Biophys* 1992; 1126:1-16.
13. Glombitza G J, Becker E, Kaiser H W, et al. Biosynthesis, processing, and intracellular transport of GM2 activator protein in human epidermal keratinocytes. The lysosomal targeting of the GM2 activator is independent of a mannose-6-phosphate signal. *J Biol Chem* 1997; 272:5199-5207.
14. Schepers U, Glombitza G, Lemm T, et al. *Molecular analysis of a GM2-activator deficiency in two patients with GM2-gangliosidosis A B variant. Am J Hum Genet* 1996; 59:1048-1056.
15. Peterson P A. Characteristics of a vitamin A-transporting protein complex occurring in human serum. *J Biol Chem* 1971; 246:34-43.
16. Birklé S, Zeng G, Gao L, et al. Role of tumor-associated gangliosides in cancer progression. *Biochimie* 2003; 85:455-463.
17. Potapenko M, Shurin G V, de Leon J. Gangliosides as immunomodulators. *Adv Exp Med Biol* 2007; 601:195-203.
18. Valentino L A, Ladisch S. Localization of shed human tumor gangliosides: association with serum lipoproteins. *Cancer Res* 1992; 52:810-814.
19. Hakomori S. Tumor malignancy defined by aberrant glycosylation and sphingo(glyco)lipid metabolism. *Cancer Res* 1996; 56:5309-5318.
20. Hakomori S. Glycosynapses: microdomains controlling carbohydrate-dependent cell adhesion and signaling. *An Acad Bras Cienc* 2004; 76:553-572.
21. Mountain C F (2000) The international system for staging lung cancer. SeminSurgOncol 18: 106-115.
22. Tsim S, O'Dowd C A, Milroy R, et al. Staging of non-small cell lung cancer (NSCLC): a review. *Respir Med* 2010; 104:1767-1774.
23. Dennis J W, Granovsky M, Warren C E (1999) Protein glycosylation in development and disease. Bioessays 21: 412-421.
24. Meany D L, Chan D W (2011) Aberrant glycosylation associated with enzymes as cancer biomarkers. Clin Proteomics 8: 7.
25. Dennis J W, Granovsky M, Warren C E (1999) Glycoprotein glycosylation and cancer progression. BiochimBiophysActa 1473: 21-34.
26. Dennis J W, Laferte S, Waghorne C, Breitman M L, Kerbel R S (1987) Beta 1-6 branching of Asn-linked oligosaccharides is directly associated with metastasis. Science 236: 582-585.
27. Black P H. Shedding from normal and cancer-cell surfaces. *N Engl J Med* 1980; 303:1415-1416.
28. Ladisch S, Gillard B, Wong C. Shedding and immuno-regulatory activity of YAC-1 lymphoma cell gangliosides. *Cancer Res* 1983; 43:3808-3813.
29. Skipksi V P, Katopodis N, Prendergast J S, et al. Gangliosides in blood serum of normal rats and Morris hepatoma 5123tc-bearing rats. *Biochem Biophys Res Commun.* 1975; 67:1122-1127.
30. Kloppel T M, Keenan T W, Freeman M J, et al. Glycolipidbound sialic acid in serum: increased levels in mice and humans bearing mammary carcinomas. *Proc Natl Acad Sci USA* 1977; 74:3011-3013.
31. Ladisch S, Wu Z L. Detection of a tumor-associated ganglioside in plasma of patients with neuroblastoma. *Lancet* 1985; 1:136-138.
32. Li R X, Ladisch S. Shedding of human neuroblastoma gangliosides. *Biochim Biophys Acta* 1991; 1083:57-64.
33. Offner H, Thieme T, Vandenbark A A. Gangliosides induce selective modulation of CD4 from helper T lymphocytes. *J Immunol* 1987; 139:3295-3305.
34. Chu J W, Sharom F J, Gangliosides interact with interleukin-4 and inhibit interleukin-4-stimulated helper T-cell proliferation. *Immunology* 1995; 84:396-403.
35. Grayson G, Ladisch S. Immunosuppression by human gangliosides II. Carbohydrate structure and inhibition of human N K activity. *Cell Immunol* 1992; 139:18-29.
36. Higashi K, Kubo H, Watanabe H, et al. Adipokine ganglioside G M activator protein stimulates insulin secretion. *FEBB Letters* 2011; 585:2587-2591.
37. Rigata B, Yeger H, Shehnaz D, et al. GM2 activator protein inhibits platelet activating factor signaling in rats. *Biochem Biophys Res* 2009; 385:576-580.

What is claimed is:

1. A method for diagnosing and treating early stage lung cancers, comprising the following steps:
   (1) providing a sample from a patient, wherein said sample is a urine sample or a serum sample;
   (2) detecting the amount of a lung cancer biomarker in said sample, wherein the lung cancer biomarker comprises a GM2-activator protein (GM2AP) protein represented by SEQ ID NO: 1 or SEQ ID NO: 2;
   (3) assessing the amount of the lung cancer biomarker in said sample to diagnose whether the patient suffers from an early stage lung cancer or predict the lung cancer prognosis of the patient, wherein when the amount of the lung cancer biomarker in the urine sample or the serum sample of the patient is higher than a standard of a random selected subset of normal population, the patient is diagnosed as suffering from an early stage lung cancer, wherein the early stage is stage I or stage II; and
   (4) administering a lung cancer treatment to the patient.

2. The method according to claim 1, wherein the step (2) is detected by immunoanalysis or mass spectrometry.

3. The method according to claim 2, wherein the immunoanalysis comprises Western blotting, flow cytometry, immunohistochemistry staining, or ELISA.

4. The method according to claim 2, wherein the mass spectrometry is processed through multiple reaction monitoring by a mass spectrometer for relative quantification.

5. The method according to claim 1, wherein when the IHC score of said lung cancer biomarker in lung tissue section of a lung cancer patient is 2, the lung cancer patient has a worse prognosis.

6. The method according to claim 5, wherein the lung cancer patient suffers from an early stage non-small cell lung cancer.

7. The method according to claim 1, wherein the standard of the random selected subset of normal population for the urine sample is 0.234 ng/mL.

8. The method according to claim 1, wherein the standard of the random selected subset of normal population for the serum sample is 0.342 ng/mL.

9. A method for diagnosing and treating early stage lung cancers, comprising the following steps:
   (a) obtaining a first sample of a subject; detecting the amount of GM2-activator protein (GM2AP) protein represented by SEQ ID NO: 1 or SEQ ID NO: 2; provided when the amount of the lung cancer biomarker in the first sample is higher than a first cut-off point, the following step (b) is conducted:
   (b) obtaining a second sample of the subject; detecting the amount of GM2-activator protein (GM2AP) protein represented by SEQ ID NO: 1 or SEQ ID NO: 2; wherein when the amount of the lung cancer biomarker in the second sample is higher than a second cut-off point, administering the subject with a lung cancer treatment,
   wherein the first sample is serum and the second sample is urine, or the first ample is urine and the second sample is serum.

10. The method for diagnosing and treating early stage lung cancers according to claim 9, wherein the cut-off point is calculated based on a random selected subset of a normal population.

* * * * *